United States Patent
Soleymani et al.

(10) Patent No.: US 10,274,453 B2
(45) Date of Patent: *Apr. 30, 2019

(54) NANOSTRUCTURED MICROELECTRODES AND BIOSENSING DEVICES INCORPORATING THE SAME

(71) Applicant: The Governing Council of the University of Toronto, Toronto (CA)

(72) Inventors: Leyla Soleymani, Toronto (CA); Zhichao Fang, Toronto (CA); Shana Kelley, Toronto (CA); Edward Sargent, Toronto (CA); Bradford Taft, San Francisco, CA (US)

(73) Assignee: The Governing Council of the University of Toronto, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/703,120

(22) Filed: Sep. 13, 2017

(65) Prior Publication Data

US 2018/0003665 A1 Jan. 4, 2018

Related U.S. Application Data

(60) Continuation of application No. 14/514,139, filed on Oct. 14, 2014, now Pat. No. 9,791,402, which is a
(Continued)

(51) Int. Cl.
*G01N 27/327* (2006.01)
*G01N 33/543* (2006.01)
*G01N 27/30* (2006.01)

(52) U.S. Cl.
CPC ......... *G01N 27/3272* (2013.01); *G01N 27/30* (2013.01); *G01N 27/3275* (2013.01);
(Continued)

(58) Field of Classification Search
CPC .. C12Q 2565/607; B82Y 15/00; B82Y 40/00; Y10S 977/924; Y10S 977/754;
(Continued)

(56) References Cited

U.S. PATENT DOCUMENTS

| 4,976,740 A | 12/1990 | Kleiner |
| 5,269,903 A | 12/1993 | Ikariyama et al. |

(Continued)

FOREIGN PATENT DOCUMENTS

| AU | 758 063 B2 | 3/2003 |
| CN | 1065527 A | 10/1992 |

(Continued)

OTHER PUBLICATIONS

R. Gasparac, et al. "Ultrasensitive Electrocatalytic DNA Detection at Two- and Three-Dimensional Nanoelectrodes" Journal of the American Chemical Society, vol. 126, p. 12270-12271 (Year: 2004).*
(Continued)

*Primary Examiner* — J. Christopher Ball

(57) ABSTRACT

Nanostructured microelectrodes and biosensing devices incorporating the same are disclosed herein.

48 Claims, 15 Drawing Sheets

Related U.S. Application Data division of application No. 13/061,465, filed as application No. PCT/CA2009/001212 on Sep. 1, 2009, now Pat. No. 8,888,969.

(60) Provisional application No. 61/093,667, filed on Sep. 2, 2008.

(52) U.S. Cl.
CPC ..... *G01N 27/3278* (2013.01); *G01N 33/5438* (2013.01); *Y10S 977/754* (2013.01); *Y10S 977/925* (2013.01)

(58) Field of Classification Search
CPC ............... Y10S 977/925; Y10S 977/92; B01J 2219/00605; G01N 33/5438; B01L 2300/0636
See application file for complete search history.

(56) References Cited

U.S. PATENT DOCUMENTS

| | | | |
|---|---|---|---|
| 5,312,527 A | 5/1994 | Mikkelsen et al. | |
| 5,340,748 A | 8/1994 | Baugher et al. | |
| 5,387,462 A | 2/1995 | Debe | |
| 5,942,388 A | 8/1999 | Willner et al. | |
| 5,968,745 A | 10/1999 | Thorp et al. | |
| 5,972,692 A | 10/1999 | Hashimoto et al. | |
| 6,123,819 A | 9/2000 | Peeters | |
| 6,180,346 B1 | 1/2001 | Thorp et al. | |
| 6,221,586 B1 | 4/2001 | Barton et al. | |
| 6,262,825 B1 | 7/2001 | Mueller et al. | |
| 6,264,825 B1 | 7/2001 | Blackburn et al. | |
| 6,300,141 B1 | 10/2001 | Segal et al. | |
| 6,325,904 B1 | 12/2001 | Peeters | |
| 6,361,951 B1 | 3/2002 | Thorp et al. | |
| 6,399,303 B1 | 6/2002 | Connolly | |
| 6,479,240 B1 | 11/2002 | Kayyem et al. | |
| 6,593,090 B2 | 7/2003 | Connolly | |
| 6,620,625 B2 | 9/2003 | Wolk et al. | |
| 6,653,625 B2 | 11/2003 | Andersson et al. | |
| 6,761,816 B1 | 7/2004 | Blackburn et al. | |
| 6,846,654 B1 | 1/2005 | Blackburn et al. | |
| 6,977,151 B2 | 12/2005 | Kayyem et al. | |
| 7,056,669 B2 | 6/2006 | Kayyem et al. | |
| 7,202,028 B2 | 4/2007 | Thorp et al. | |
| 7,361,470 B2 | 4/2008 | Kelley et al. | |
| 7,361,471 B2 | 4/2008 | Gerdes et al. | |
| 7,381,525 B1 | 6/2008 | Kayyem et al. | |
| 7,741,033 B2 | 6/2010 | Kelly et al. | |
| 7,879,554 B2 | 2/2011 | Crothers et al. | |
| 7,892,816 B2 | 2/2011 | Elliott et al. | |
| 8,058,155 B1 | 11/2011 | Bhansali | |
| 8,221,597 B2 | 7/2012 | Lee et al. | |
| 8,318,919 B2 | 11/2012 | Crothers | |
| 8,888,969 B2 * | 11/2014 | Soleymani ......... G01N 33/5438 204/289 |
| 9,335,289 B2 | 5/2016 | Kelly et al. | |
| 9,772,329 B2 | 9/2017 | Das et al. | |
| 9,791,402 B2 * | 10/2017 | Soleymani ......... G01N 27/3272 |
| 9,816,129 B2 | 11/2017 | Kelly et al. | |
| 2002/0081588 A1 | 6/2002 | De Lumley-Woodyear et al. | |
| 2002/0084410 A1 | 7/2002 | Colbert et al. | |
| 2002/0158342 A1 | 10/2002 | Tuominen et al. | |
| 2002/0172963 A1 * | 11/2002 | Kelley ............... B01J 23/75 506/39 |
| 2002/0179457 A1 | 12/2002 | Heller | |
| 2003/0054381 A1 | 3/2003 | Affourtit | |
| 2003/0087277 A1 | 5/2003 | Fritzsche et al. | |
| 2003/0089899 A1 | 5/2003 | Lieber et al. | |
| 2003/0108938 A1 | 6/2003 | Pickar | |
| 2003/0143571 A1 | 7/2003 | Sharp et al. | |
| 2003/0152960 A1 | 8/2003 | Thorp et al. | |
| 2003/0208454 A1 | 11/2003 | Rienhoff, Jr. | |
| 2003/0211637 A1 | 11/2003 | Schoeniger et al. | |
| 2004/0002818 A1 | 1/2004 | Kulp | |
| 2004/0005582 A1 | 1/2004 | Shipwash | |
| 2004/0040840 A1 | 3/2004 | Mao et al. | |
| 2004/0072263 A1 | 4/2004 | Link et al. | |
| 2004/0106203 A1 | 6/2004 | Stasiak et al. | |
| 2004/0114445 A1 | 6/2004 | Occhipinti et al. | |
| 2004/0136866 A1 | 7/2004 | Pontis et al. | |
| 2005/0064476 A1 | 3/2005 | Huang | |
| 2005/0084881 A1 * | 4/2005 | Kelley ................. C12Q 1/6825 435/6.11 |
| 2005/0118731 A1 | 6/2005 | Salafsky | |
| 2005/0239121 A1 | 10/2005 | Gall et al. | |
| 2006/0063188 A1 | 3/2006 | Zanni et al. | |
| 2006/0160100 A1 | 7/2006 | Gao et al. | |
| 2006/0204738 A1 | 9/2006 | Dubrow et al. | |
| 2007/0082351 A1 | 4/2007 | Stender et al. | |
| 2007/0099211 A1 | 5/2007 | Aivazachvili et al. | |
| 2007/0154909 A1 | 7/2007 | Xiao et al. | |
| 2007/0187840 A1 | 8/2007 | Dell'AcquaBellavitis | |
| 2008/0081329 A1 | 4/2008 | Elliott et al. | |
| 2008/0185295 A1 * | 8/2008 | Briman .............. G01N 33/5438 205/777.5 |
| 2009/0061451 A1 | 3/2009 | Achim et al. | |
| 2009/0186345 A1 | 7/2009 | Yamashita et al. | |
| 2009/0254093 A1 | 10/2009 | White et al. | |
| 2009/0270266 A1 | 10/2009 | Kelley et al. | |
| 2009/0283425 A1 | 11/2009 | Clark et al. | |
| 2009/0288960 A1 | 11/2009 | Rubin et al. | |
| 2009/0308744 A1 | 12/2009 | Nam et al. | |
| 2010/0041077 A1 | 2/2010 | Nagy et al. | |
| 2010/0207602 A1 | 8/2010 | Loverich | |
| 2010/0282617 A1 | 11/2010 | Rothberg et al. | |
| 2012/0067742 A1 | 3/2012 | Lee et al. | |
| 2012/0073987 A1 | 3/2012 | Kraatz et al. | |
| 2014/0342359 A1 | 11/2014 | Kelly et al. | |
| 2018/0163257 A1 | 6/2018 | Kelly et al. | |
| 2018/0188244 A1 | 7/2018 | Das et al. | |

FOREIGN PATENT DOCUMENTS

| | | |
|---|---|---|
| CN | 101268199 A | 9/2008 |
| CN | 101306794 A | 11/2008 |
| CN | 102216762 A | 10/2011 |
| EP | 0 564 254 A | 10/1993 |
| EP | 1 629 122 B1 | 3/2006 |
| EP | 1 784 512 A2 | 5/2007 |
| EP | 1 806 414 A2 | 7/2007 |
| EP | 2 163 653 A2 | 3/2010 |
| EP | 2 261 648 A1 | 12/2010 |
| JP | H07301615 A | 11/1995 |
| JP | H 10267888 A | 10/1998 |
| JP | 2000-505890 | 5/2000 |
| JP | 2003-322653 A | 11/2003 |
| JP | 2005-164388 A | 6/2005 |
| JP | 2005-227145 A | 8/2005 |
| JP | 2006-030027 A | 2/2006 |
| JP | 2007-139730 A | 6/2007 |
| JP | 2007-187531 A | 7/2007 |
| JP | 2008-527392 A | 7/2008 |
| JP | 5-188013 B2 | 4/2013 |
| WO | WO 92/17774 A1 | 10/1992 |
| WO | WO 92/21980 A1 | 12/1992 |
| WO | WO 96/06946 A1 | 3/1996 |
| WO | WO 97/27474 A1 | 7/1997 |
| WO | WO 99/38007 A1 | 7/1999 |
| WO | WO 99/67425 A2 | 12/1999 |
| WO | WO 99/67628 A1 | 12/1999 |
| WO | WO 00/52456 A1 | 9/2000 |
| WO | WO 02/074988 A2 | 9/2002 |
| WO | WO 02/079514 A1 | 10/2002 |
| WO | WO 2003/049592 A2 | 6/2003 |
| WO | WO 03/091455 A1 | 11/2003 |
| WO | WO 2004/027093 A1 | 4/2004 |
| WO | WO 2004/079331 A2 | 9/2004 |
| WO | WO 2005/005952 A2 | 2/2005 |
| WO | WO 2006/076047 A2 | 7/2006 |
| WO | WO 2006/094200 A2 | 9/2006 |
| WO | WO 2007/094805 A2 | 8/2007 |
| WO | WO 2008/018833 A1 | 2/2008 |

(56) References Cited

FOREIGN PATENT DOCUMENTS

| WO | WO 2008/045799 A2 | 4/2008 |
|---|---|---|
| WO | WO 2008/068752 A2 | 6/2008 |
| WO | WO 2009/032901 A1 | 3/2009 |
| WO | WO 2010/025547 A1 | 3/2010 |
| WO | WO 2010/107058 A1 | 9/2010 |

OTHER PUBLICATIONS

F. Gao, et al. "Electrochemical Preparation of a Au Crystal with peculiar Morphology and Unique Growth Orientation and Its Catalysis for Oxygen Reduction", Journal of the Electrochemical Society, vol. 152, No. 6, p. A1226-1232 (Year: 2005).*
Aoki et al., "Trace analysis of an oligonucleotide with a specific sequence using PNA-based ion-channel sensors," The Analyst 2003; 128(6):681-685.
Armani et al., "Label-free, single-molecule detection with optical microcavities," Science 2007; 317(5839):783-787.
Armistead et al., "Electrochemical Detection of Gene Expression in Tumor Samples: Overexpression of Rak Nuclear Tyrosine Kinase," Bioconj Chem. 2002; 13:172-176.
Bard et al., "Electrochemical Methods: Fundamentals and Applications," Chapter 3: Kinetics of Electrode Reactions, Wiley, New York 2000; pp. 87-136.
Beaucage et al., "Deoxynucleoside phosphoramidites—A new class of key intermediates for deoxypolynucleotide synthesis," Tetrahedron Lett. 1981; 22(20):1859-1862.
Blaser, "Helicobacter pylori and the pathogenesis of gastroduodenal inflammation," J Infect Dis. 1990; 161(4):626-633. Review.
Bond et al., "Steady-state voltammetry," Anal Chim Acta. 1989; 216:177-230.
Boon et al., "Mutation detection by electrocatalysis at DNA-modified electrodes," Nat Biotech. 2000; 18:1096-1100.
Brunetti et al., "Electrochemistry of phenothiazine and methylviologen biosensor electronic-transfer ensembles," J. Electroanal. Chem. 2000; 491:166-174.
Cheng et al., "Ultramicroelectrode ensembles. Comparison of experimental and theoretical responses and evaluation of electroanalytical detection limits," Anal Chem. 1989; 61(7):762-766.
Chilvers et al., "Phototoxicity of rose bengal in mycological media—implications for laboratory practice," Lett Appl Microbiol. Feb. 1999; 28(2):103-107.
Clack et al., "Electrostatic readout of DNA microarrays with charged microspheres," Nature Biotechnol. 2008; 26:825-830.
Coche-Guerente et al., "Amplification of amperometric biosensor responses by electrochemical substrate recycling. 3. Theoretical and experimental study of the phenol-polyphenol oxidase system immobilized in Laponite hydrogels and layer-by-layer self-assembled structures," Anal Chem. Jul. 15, 2001; 73(14):3206-3218.
Conlon et al., "Site-directed photochemical disruption of the actin cytoskeleton by actin-binding Rose Bengal-conjugates," J Photochem Photobiol B. Nov. 2002; 68(2-3):140-146.
Drmanac et al., "Determination by hybridization: a strategy for efficient large-scale sequencing," Science 1993; 260(5114):1649-1652.
Drummond et al., "Electrochemical DNA Sensors," Nature Biotechnol. 2003; 21:1192-1199.
Egholm et al., "Peptide Nucleic Acids (PNA). Oligonucleotide Analogues with an Achiral Peptide Backbone," J. Amer. Chem. Soc. 1992; 114(5):1895-1897.
Esteva et al., "Clinical utility of serum HER2/neu in monitoring and prediction of progression-free survival in metastatic breast cancer patients treated with trastuzumab-based therapies," Breast Cancer Res. 2005; 7(4):4347-4353.
European Search Report dated Aug. 12, 2015 for European Application No. 14176968.7, 5 pages.
European Search Report dated Oct. 26, 2017 for European Application No. 17165963.4, 9 pages.
Examination Report dated Jan. 16, 2013 for Canadian Application No. 2,735,735, 2 pages.
Examination Report dated Jan. 16, 2017 for European Application No. 12734237.6, 5 pages.
Examination Report dated Mar. 28, 2013 for European Application No. 09810953.1, 4 pages.
Extended European Search Report dated Jan. 11, 2010 for European Application No. 05856910.4, 9 pages.
Extended European Search Report dated Jan. 11, 2012 for European Application No. 09810953.1, 6 pages.
Extended European Search Report dated Jun. 14, 2018 for European Application No. 17207095.5, 12 pages.
Extended European Search Report dated Mar. 28, 2017 for European Application No. 16185746.1, 13 pages.
Extended European Search Report dated May 6, 2015 for European Application No. 12851735.6, 8 pages.
Extended European Search Report dated May 8, 2015 for European Application No. 12734237.6, 8 pages.
Extended European Search Report dated Oct. 16, 2014 for European Application No. 14176968.7, 7 pages.
Extended European Search Report dated Sep. 12, 2014 for European Application No. 12744938.7, 8 pages.
Fang et al., "Direct electrocatalytic mRNA detection using PNA-nanowire sensors," Anal. Chem. 2009; 81(2):612-617.
Ferain et al., "Track-etch templates designed for micro- and nanofabrication," Nucl Instrum Meth Phys Res. Sec B; 2003; 208:115-122.
Ferreira et al., "Electrochemical and spectroscopic characterization of screen-printed gold-based electrodes modified with self-assembled monolayers and Tc85 protein," Journal of Electr. Chemistry 2009; 634(2):111-122.
Final Office Action dated Apr. 19, 2017 for U.S. Appl. No. 15/091,369, 5 pages.
Final Office Action dated Feb. 12, 2014 for U.S. Appl. No. 13/061,465, 12 pages.
Final Office Action dated Jun. 14, 2016 for U.S. Appl. No. 14/360,528, 19 pages.
Final Office Action dated Mar. 31, 2009 for U.S. Appl. No. 10/913,925, 24 pages.
Finot et al., "Performance of interdigitated nanoelectrodes for electrochemical DNA biosensor," Ultramiscroscopy 2003; 97(1-4):441-449.
First Examination Report dated Feb. 1, 2017 for Indian Application No. 2307/DELNP/2011, 9 pages.
First Office Action dated Jun. 3, 2015 for Chinese Application No. 201280067868.2, 6 pages.
First Office Action dated Mar. 5, 2013 for Chinese Application No. 200980143689.0, with English translation, 25 pages.
Fleury, "Branched fractal patterns in non-equilibrium electrochemical deposition from oscillatory nucleation and growth," Nature 1997; 390:145-148.
Forrer et al., "Electrochemical preparation and surface properties of gold nanowire arrays formed by the template technique," J. Appl. Electrochem. 2000; 30:533-541.
Fourth Office Action dated Mar. 9, 2015 for Chinese Application No. 200980143689.0, with English translation, 25 pages.
Fukami et al., "General mechanism for the synchronization of electrochemical oscillations and self-organized dendrite electrodeposition of metals with ordered 2D and 3D microstructures," J. Phys. Chem. C 2007; 111:1150-1160.
Geiss et al., "Direct multiplexed measurement of gene expression with color-coded probe pairs," Nat. Biotechnol. 2008; 26(3):317-325.
Geng et al., "Self-assembled monolayers-based immunosensor for detection of *Escherichia coli* using electrochemical impedance spectroscopy," Electrochimica ACTA 2008; 53(14):4663-4668.
Gooding et al., "Protein electrochemistry using aligned carbon nanotube arrays," J Am Chem Soc Jul. 30, 2003; 125(30):9006-9007.
Gore et al., "Detection of attomole quantities [correction of quantities] of DNA targets on gold microelectrodes by electrocatalytic nucleobase oxidation," Anal chem Dec. 1, 2003; 75(23):6586-6592.

(56) References Cited

OTHER PUBLICATIONS

Hacia et al., "Detection of heterozygous mutations in BRCA1 using high density oligonucleotide arrays and two-colour fluroescence analysis," Nat. Genet. 1996; 14:441-447.
Hahm et al., "Direct ultrasensitive electrical detection of DNA and DNA sequence variations using nanowire nanosensors," Nano Lett. 2004; 4:51-54.
Handbook of Electrochemistry, Cynthia G. Zoski, ed., Elsevier 2006; pp. 391-428.
Hashimoto et al., "Novel DNA sensor for electrochemical gene detection," Anal. Chem. 1994; 286:219-224.
Hashimoto et al., "Sequence-Specific Gene Detection with a Gold Electrode Modified with DNA Probes and an Electrochemically Active Dye," Anal. Chem; 1994; 66:3830-3833.
Heaton et al., "Electrostatic surface plasmon resonance: direct electric field-induced hybridization and denaturation in monolayer nucleic acid films and label-free discrimination of base mismatches," Proc Natl Acad Sci USA 2001; 98(7):3701-3704. Epub 2001.
Heinze, "Ultramicroelectrodes in electrochemistry," Angew. Chem. Int. Ed. 1993; 32:1268-1288.
Hrapovic et al., "Reusable platinum nanoparticle modified boron doped diamond microelectrodes for oxidative determination or arsenite," Anal. Chem. 2007; 79:500-507.
Hu et al., "Capacitive immunosensor for transferrin based on o-aminobenzenthiol oligomer layer," Analytica Chimica Acta. 2002; 459(2):297-304.
International Preliminary Report on Patentability dated Mar. 8, 2011 for International Application No. PCT/CA2009/001212, 6 pages.
International Search Report and Written Opinion dated Aug. 28, 2012 for International Application No. PCT/US2012/020965, 10 pages.
International Search Report and Written Opinion dated Jul. 13, 2012 for International Application No. PCT/US2012/024015, 9 pages.
International Search Report and Written Opinion dated Mar. 1, 2013 for International Application No. PCT/US2012/066410, 18 pages.
International Search Report and Written Opinion dated Oct. 31, 2012 for International Application No. PCT/US2012/028721, 6 pages.
International Search Report dated Dec. 10, 2009 for International Application No. PCT/CA2009/001212, 3 pages.
International Search Report dated mailed Feb. 22, 2008 for International Application No. PCT/US2005/27710, 2 pages.
International Search Report dated Jun. 24, 2005 for International Application No. PCT/US2004/014788, 1 page.
Jagotamoy et al., "A Nanocatalyst-Based Assay for Proteins: DNA-Free Ultrasensitive Electrochemical Detection Using Catalytic Reduction of p-Nitrophenol by Gold-Nanoparticle Labels," Journal of the American Chemical Society 2006; 128(50):10622-16023.
Katz et al., "Electroanalytical and bioelectroanalytical systems based on metal and semiconductor nanoparticles," Electroanalysis 2004; 16:19-44.
Katz et al., "Probing biomolecular interactions at conductive and semiconductive surfaces by impedance spectroscopy: routes to impedimetric immunosensors, DNA-sensors, and enzyme biosensors," Electroanalysis 2003; 15:913-947.
Ke et al., "Self-assembled water-soluble nucleic acid probe tiles for label-free RNA hybridization assays," Science 2008; 319:180-183.
Kelley et al., "Single-base mismatch detection based on charge transduction through DNA," Nucleic Acids Research 1999; 27(4):4830-4837.
Kim et al., "Microfluidic Sample Preparation: Cell Lysis and Nucleic Acid Purification," Integrative Biology 2009; 1(10):574-586.
Koehne et al., "Ultrasensitive label-free DNA analysis using an electronic chip based on carbon nanotube nanoelectrode arrays," Nanotechnology 2003; 14(12):1239-1245.
Koppelhus et al., "Cell-Dependent Differential Cellular Uptake of PNA, Peptides, and PNA-Peptide Conjugates," Antisense & Nucleic Acid Drug Development 2002; 12(2):51-63.
Lam et al., "Polymerase Chain Reaction-Free, Sample-to-Answer Bacterial Detection in 30 Minutes with Integrated Cell Lysis," Analytical Chemistry 2011; 84(1):21-25.
Lapierre et al., "Electrocatalytic detection of pathogenic DNA sequences and antibiotic resistance markers," Anal Chem. Nov. 15, 2003; 75(22):6327-6333.
Lapierre-Devlin et al., "Amplified electrocatalysis at DNA-modified nanowires," Nano Lett. 2005; 5(6):1051-1055.
Lee, "Tris 2,2' bipyridyl ruthenium electrogenerated chemiluminescence in analytical science," Mikrochim. Acta 1997; 127(1-2):19-39.
Li et al., "Carbon nanotube nanoelectrode array for ultrasensitive DNA detection," Nanoletters 2003; 3:597-602.
Li et al., "Fabrication approach for molecular memory arrays," Appl Phys Lett. 2003; 82(4):645-647.
Li et al., "Highly-ordered carbon nanotube arrays for electronics applications," Appl Phys Lett. 1999; 75:367.
Liu et al., "Voltammetric determination of sequence-specific DNA by electroactive intercalator on graphite electrode," Anal Chem. 1996; 335:239-243.
Lu et al., "Three Dimensional Electrode Array for Cell Lysis Via Electroporation," Biosensors and Bioelectronics 2006; 22(4):568-574.
Malaquin et al., "Nanoelectrode-based devices for electrical biodetection in liquid solution," Microelect Eng. 2004; 73-74:887-892.
Martin et al., "Nanomaterials in analytical chemistry," Analytical Chemistry News & Features 1998; pp. 322A-327A.
Maruyama et al., "Detection of target DNA by electrochemical method," Sensor and Actuators B 2001; 76:215-219.
Matysik, "Miniaturization of electroanalytical Systems," Anal. Bioanal. Chem. 2003; 375(1):33-35.
McGuire et al., "The future of personal genomics," Science 2007; 317(5845):1687.
Meinkoth et al., "Hybridization of nucleic acids immobilized on solid supports," Anal. Biochem. 1984; 138:267-284.
Menke et al., "Lithographically patterned nanowire electrodeposition," Nature 2006; 5:914-919.
Menon et al., "Fabrication and Evaluation of Nanoelectrode Ensembles," Anal Chem. 1995; 67:1920-1928.
Milian et al., "Sequence-Selective Biosensor for DNA Based on Electroactive Hybridization Indicators," Anal. Chem. 1993; 65:2317-2323.
Mirkin et al, "A DNA-based method for rationally assembling nanoparticles into macroscopic materials," Nature 1996; 382(6592):607-609.
Moretto et al., "Voltammetry of redox analytes at trace concentrations with nanoelectrode ensembles," Talanta 2004; 62:1055-1060.
Morris et al., "Gene expression profiling in breast cancer," Curr. Opin. Oncol. 2007; 19:547-551.
Munge et al., "Multiple enzyme layers on carbon nanotubes for electrochemical detection down to 80 DNA copies," Anal. Chem. 2005; 77:4662-4666.
Napier et al., Probing Biomolecule Recognition with Electron Transfer: Electrochemical Sensors for DNA Hybridization, Bioconj Chem. 1997; 8:906-913.
Nelson et al., "Label-free detection of 16S ribosomal RNA hybridization on reusable DNA arrays using surface plasmon resonance imaging," Environ Microbiol. 2002; 4(11):735-743.
Nelson et al., "Surface plasmon resonance imaging measurements of DNA and RNA hybridization adsorption onto DNA microarrays," Anal Chem. 2001; 73(1):1-7.
Nicewarner-Pena et al., "Submicrometer metallic barcodes," Science 2001; 294:137-141.
Non-Final Office Action dated Dec. 22, 2015 for U.S. Appl. No. 14/360,528, 16 pages.
Non-Final Office Action dated Apr. 19, 2017 for U.S. Appl. No. 14/360,528, 20 pages.
Non-Final Office Action dated Aug. 22, 2013 for U.S. Appl. No. 13/061,465, 10 pages.
Non-Final Office Action dated Aug. 27, 2007 for U.S. Appl. No. 10/913,928, 22 pages.
Non-Final Office Action dated Feb. 19, 2016 for U.S. Appl. No. 13/978,372, 8 pages.

(56) References Cited

OTHER PUBLICATIONS

Non-Final Office Action dated Jan. 25, 2007 for U.S. Appl. No. 10/913,928, 18 pages.
Non-Final Office Action dated Jul. 29, 2016 for U.S. Appl. No. 15/091,369, 9 pages.
Non-Final Office Action dated Jun. 18, 2008 for U.S. Appl. No. 10/913,928, 25 pages.
Non-Final Office Action dated Jun. 4, 2015 for U.S. Appl. No. 13/983,934, 8 pages.
Non-Final Office Action dated Mar. 21, 2008 for U.S. Appl. No. 11/270,983, 2 pages.
Non-Final Office Action dated Mar. 29, 2018 for U.S. Appl. No. 15/726,676, 6 pages.
Non-Final Office Action dated May 31, 2007 for U.S. Appl. No. 11/270,983, 10 pages.
Non-Final Office Action dated Oct. 4, 2016 for U.S. Appl. No. 14/514,139, 13 pages.
Non-Final Office Action dated Sep. 30, 2016 for U.S. Appl. No. 13/978,372, 12 pages.
Notice of Final Rejection dated Jul. 25, 2014 for Japanese Application No. 2011-524152, 3 pages.
Notice of Reasons for Rejection dated Aug. 24, 2015 for Japanese Application No. 2013-549519, 4 pages.
Notice of Reasons for Rejection dated Nov. 17, 2017 for Japanese Application No. 2016-033918, 4 pages.
Notification of Reasons of Refusal dated Dec. 10, 2013 for Japanese Application No. 2011-524152, 3 pages.
Notification of Reasons of Refusal dated Mar. 13, 2013 for Japanese Application No. 2011-524152, 2 pages.
Notterman et al., "Tumor Biology and Microarray Analysis of Solid Tumors: Colorectal Cancer as a Model System," Microarrays and Cancer Research 2002; Warrington et al., (eds.), Eaton Publishing, Westborough, MA, pp. 81-111.
Office Action dated Jun. 20, 2016 for Russian Application No. 2013137419, w/English translation, 10 pages.
Online definition of "ensemble," Oxford Dictionary (American English), <www.oxforddictionaries.com/us/definition/american_english/ensemble>, accessed on Feb. 5, 2014.
Palecek et al., "Electrochemical biosensors for DNA hybridization and DNA damage," Biosens Bioelectron. 1998; 13:621-928.
Pan et al., "Electrochemical Immunosensor Detection of Urinary Lactoferrin in Clinical Samples for Urinary Tract Infection Diagnosis," Biosensors and Bioelectronics 2010; 26(2):649-654.
Park et al., "Array-based electrical detection of DNA with nanoparticle probes," Science 2002; 295:1503-1506.
Patolsky et al., "Electronic Transduction of Polymerase or Reverse Transcriptase Induced Replication Processes on Surfaces: Highly Sensitive and Specific Detection of Viral Genomes," Angew Chem Int Ed Engl. Jun. 18, 2001; 40(12):2261-2265.
Patolsky et al., "Nanowire-Based Biosensors," Analytical Chemistry, Jul. 1, 2006; 4261-4269.
Peterson et al., "Hybridization of mismatched or partially matched DNA at surfaces," J Am Chem Soc. 2002; 124(49):14601-14607.
Peterson et al., "The effect of surface probe density on DNA hybridization," Nucleic Acids Res. 2001; 29(24):5163-5168.
Pivodori et al., "Electrochemical genosensor design: immobilisation of oligonucleotides onto transducer surfaces and detection methods," Biosens Bioelectron. 2000; 15(5-6):291-303.
Ratilainen et al., "Thermodynamics of sequence-specific binding of PNA to DNA," Biochemistry 2000; 39:7781-7791.
Reimers, "Applications of microelectrodes to problems in chemical oceanography," Chem. Rev. 2007; 107(2):590-600.
Rogers et al., "Using an elastomeric phasemask for sub-100 nm photolithography in the optical near field," Appl. Phys. Lett. 1997; 70:2658-2660.
Ropp et al., "Site-selective electron transfer form purines to electrocatalysts: voltammetric detection of a biologically relevant deletion in hybridized DNA duplexes," Chem Biol. 1999; 6:599-605.
Saiki et al., "Enzymatic amplification of β-globin genomic sequences and restriction site analysis for diagnosis of sickle cell anemia," Science 1985; 230(4732):1350-1354.
Search and Examination Report dated Dec. 2, 2011 for Singapore Application 200903655-9, 6 pages.
Second Office Action dated Apr. 5, 2016 for Chinese Application No. 201280067868.2, 5 pages.
Second Office Action dated Jan. 13, 2014 for Chinese Application No. 200980143689.0, with English translation, 14 pages.
Shi, "Technologies for individual genotyping: detection of genetic polymorphisms in drug targets and disease genes," Am J Pharmacogenomics 2002; 2(3):197-205. Review.
Silvester et al., "Effect of terminal amino acids on the stability and specificity of PNA-DNA hybridisation," Organic & Biomolecular Chemistry 2007; 5(6):917-923.
Sinensky et al., "Label-free and high-resolution protein/DNA nanoarray analysis using Kelvin probe force microscopy," Nat. Nanotech. 2007; 2:653-659.
Smalley, "Chip senses trace DNA," Jul. 30-Aug. 6, 2003; TRN Mag.com, 2 pages.
Smith et al., "Theory of the voltammetric response of electrodes of submicron dimensions. Violation of electroneutrality in the presence of excess supporting electrolyte," Anal Chem. 1993; 65(23):3343-3353.
Soleymani et al., "Nanostructuring of patterned microelectrodes to enhance the sensitivity of electrochemical nucleic acids detection," Angewandte Chemie—International Edition Oct. 26, 2009 Wiley-VCH Verlag DEU, vol. 48, No. 45, Oct. 26, 2009, pp. 8457-8460.
Soleymani et al., "Parallel detection of nucleic acids using an electronic chip," Innovations in Information Technology, 2008. IIT 2008. International Conference on IEEE, Piscataway, NJ, USA, Dec. 16, 2008, pp. 20-23.
Southern, "DNA Microarrays. History and Overview," Methods Mol Biol. 2001; 170:1-15. Review.
Srinivas et al., "Trends in biomarker research for cancer detection," Lancet Oncol. 2001; 11:698-704.
Steel et al., "Electrochemical Quantitation of DNA Immobilized on Gold," Anal Chem. 1998; 70:4670-4677.
Steemers et al., "Screening unlabeled DNA targets with randomly ordered fiber-optic gene arrays," Nat. Biotechnol. 2000; 18:91-94.
Strausberg et al., "Reading the Molecular Signatures of Cancer," Microarrays and Cancer Research 2002; Warrington et al. (eds.), Eaton Publishing, Westborough, MA, pp. xi-xvi.
Stulik et al., "Microelectrodes. Definitions, Characterizations, and Applications," Pure and Applied Chemistry 2000; 72(8): 1483-1492.
Supplementary European Search Report dated Nov. 26, 2007 for European Application No. 04775984.0, 4 pages.
Szamocki et al., "Macroporous ultramicroelectrodes for improved electroanalytical measurements," Anal. Chem. 2007; 79:533-539.
Taft et al., "Engineering DNA-electrode connectivities: manipulation of linker length and structure," Analytica Chimica Acta. Oct. 31, 2003; 496(1-2):81-91.
Taton et al., "Scanometric DNA array detection with nanoparticle probes," Science. 2000; 289(5485):1757-1760.
Third Office Action dated Aug. 29, 2014 for Chinese Application No. 200980143689.0, 13 pages.
Thorp, Cutting out the middleman: DNA biosensors based on electrochemical oxidation, Trends in Biotechnology 1998; 16:117-121.
Tomioka et al., "A Multiplex Polymerase Chain Reaction Microarray Assay to Detect Bioterror Pathogens in Blood," The Journal of Molecular Diagnostics 2005; 7(4):486-494.
Tomlins et al., Recurrent fusion of TMPRSS2 and ETS transcription factor genes in prostate cancer, Science 2005; 310(5748):644-648.
Ueno et al., "Fabrication and electrochemical characterization of interdigitated nanoelectrode arrays," Electrochemistry Communications 2005; 7(2):161-165.
Van Gerwen et al., "Nanoscaled interdigitated electrode arrays for biochemical sensors," Sensors and Actuators 1998; B 49:73-80.
Vercoutere et al., "Biosensors for DNA sequence detection," Curren Op. in Chem. Biol. 2002; 6:816-822.

(56) References Cited

OTHER PUBLICATIONS

Wang et al., "A Microfluidic Flow-Through Device for High Throughput Electrical Lysis of Bacterial Cells Based on Continuous De Voltage," Biosensors and Bioelectronics 2006; 22(5):582-588.

Wang et al., "Electroactive beads for ultrasensitive DNA detection," Langmuir 2003; 19(4):989-991.

Wang et al., "Origins of high sequence selectivity: a stopped-flow kinetics study of DNA/RNA hybridization by duplex- and triplex-forming oligonucleotides," Biochemistry 1995; 34(30):977497-977484.

Wang et al., "Sensing Arrays Constructed from Nanoparticle thin Films and Interdigitated Microelectrodes," Sensors 2006; 6:667-679.

Wang, "From DNA biosensors to gene chips," Nucleic Acids Res. 2000; 28(16):3011-3016.

Wang, "Survey and Summary from DNA biosensors to gene chips," Nucleic Acids Research 2000; 28(16):3011-3016.

Welch et al., "The use of nanoparticles in electroanalysis: a review," Anal. Bioanal. Chem. 2006; 384:601-619.

Xiao et al., "Label-free Electrochemical detection of DNA in blood serum via target-induced resolution of an electrode-bound DNA pseudoknot," J. Am. Chem. Soc. 2007; 129(39):11896-11897.

Xu et al., "Immobilization of DNA on an Aluminum(III) Alkanebisphosphonate Thin Film with Electrogenerated Chemiluminescent Detection," J Am Chem Soc. 1994; 116:8386-8387.

Yang et al., "Direct, Electronic MicroRNA Detection for the Rapid Determination of Differential Expression Profiles," Angewandte Chemic International Edition 2009; 48(45):8461-8464.

Yang et al., "Interdigitated Array Microelectrode-Based Electrochemical Impedance Immunosensor for Detection of *Escherichia coli* O157:H7," American Chemical Society 2004; 76(4):1007-1113.

Yi et al., "Theoretical and experimental study towards nanogap dielectric biosensor," Biosens. Bioelectron. 2005; 20:1320-1326.

Yu et al., "Nano Wheat Fields Prepared by Plasma-Etching gold Nanowire-Containing Membranes," Nano Lett. 2004; 3:815-818.

Yun, Y. et al., "A nanotube array immunosensor for direct electrochemical detection of antigen-antibody binding," Sensors and Actuators 2007; B123:177-182.

Zeng et al., "Nanostructures and molecular force bases of a highly sensitive capacitive immunosensor," Proteomics 2005; 5(17):4347-4353.

Zhang et al., "Detection of ~$10^3$ copies of DNA by an electrochemical enzyme-amplified sandwich assay with ambient $O_2$ as the substrate," Anal. Chem. 2004; 76:4093-4097.

Zhang et al., "Rapid and label-free nanomechanical detection of biomarker transcripts in human RNA," Nat. Nano. 2006; 1:214-220.

\* cited by examiner

NANOSTRUCTURED MICROELECTRODES AND BIOSENSING DEVICES INCORPORATING THE SAME

CROSS-REFERENCE TO RELATED APPLICATIONS

This application is a continuation of U.S. patent application Ser. No. 14/514,139, filed on Oct. 14, 2014, which is a divisional of U.S. patent application Ser. No. 13/061,465, filed on Jun. 6, 2011, which is a United States National Stage Application filing under 35 U.S.C. § 371 of International Application No. PCT/CA2009/001212, filed on Sep. 1, 2009, which claims the benefit of priority to United States Provisional Patent Application Ser. No. 61/093,667, filed on Sep. 2, 2008, entitled Nanostructured Microelectrodes and Biosensing Devices Incorporating the Same, the contents of each of which are hereby incorporated by reference herein in their entirety. International Application No. PCT/CA2009/001212 was published under PCT Article 21(2) in English.

SEQUENCE LISTING

The instant application contains a Sequence Listing which has been submitted electronically as a text file in ASCII format and is hereby incorporated by reference in its entirety. Said text file, created on Feb. 20, 2015, is named 109904-0004-302.txt and is 6,000 bytes in size.

BACKGROUND OF THE INVENTION

Genomic analysis is revolutionizing early disease diagnosis and dramatically enhancing patient care (McGuire et al. *Science* 317:1687, Srinivas et al., *Lancet Oncol.* 2:698). Microarrays (Drmanac et al., *Science* 260:1649, Hacia et al., *Nat. Genet.* 14:441) and polymerase chain reaction (PCR)-based techniques (Saiki et al., *Science* 230:1350) have, as tools, helped to spearhead this revolution, enabling the discovery and the initial development of assays for patient testing (Morris et al., *Curr. Opin. Oncol.* 19:547). However, spreading the reach of the genomics revolution to the patient bedside demands cost effective tools for individual biomarker profiling assessed relative to a posited disease state. Specifically, tools enabling routine patient care preferably would be simpler, more portable, and less expensive than PCR-based methods, yet should retain a high degree of selectivity and sensitivity.

Biomarker analysis based on electronic readout has long been cited as a promising approach that would enable a new family of chip-based devices with appropriate cost and sensitivity for medical testing (Drummond et al., *Nat. Biotechnol.* 21:1192, Katz et al., *Electroanalysis* 15: 913). The sensitivity of electronic readout is in principle sufficient to allow direct detection of small numbers of analyte molecules with simple instrumentation. However, despite tremendous advances in this area as well as related fields working towards new diagnostics (Clack et al., *Nat. Biotechnol.* 26:825, Geiss et al., *Nat. Biotechnol.* 2:317, Hahm et al., *Nano Lett.* 4:51, Munge et al., *Anal. Chem.* 77:4662, Nicewamer-Pena et al., *Science* 294:137, Park et al., *Science* 295:1503, Sinensky et al., *Nat. Nano.* 2:653, Steemers et al., *Nat. Biotechnol.* 18:91, Xiao et al., *J. Am. Chem. Soc.* 129:11896, Zhang et al., *Nat. Nano.* 1:214, Zhang et al., *Anal. Chem.* 76:4093, Yi et al., *Biosens. Bioelectron.* 20:1320, Ke et al., *Science* 319:180, Armani et al., *Science* 317:783), current multiplexed chips have yet to achieve direct electronic detection of biomarkers in cellular and clinical samples. The challenges that have limited the implementation of such devices primarily stem from the difficulty of obtaining very low detection limits in the presence of high background noise levels present when complex biological samples are assayed, and the challenge of generating multiplexed systems that are highly sensitive and specific.

The miniaturization of electrochemical systems continues to be a major focus in analytical and bioanalytical chemistry (Matysik, *Miniaturization of Electroanalytical Systems* (Springer-Verlag, 2002)), as the attainment of enhanced sensitivity may be enabled with systems possessing micro- to nano-scale dimensions (Szamocki et al., A. *Anal. Chem.* 2007, 79, 533-539). A great deal of work has been carried out with electrodes with dimensions on the micrometer or sub-micrometer scale. These systems offer many advantages over conventional macroelectrodes such as faster double-layer charging, reduced ohmic loss, high mass-transport rates, and high current density (Bond et al. *Anal. Chimi. Acta* 1989m 216, 177-230, Heinze, *Angew. Chem. Int. Ed.* 2003, 32, 1268-1288). Indeed, such electrodes have become well-established tools in a wide range of analytical applications (Bard, *Electrochemical Methods: Fundamentals and Applications* (Wiley, New York, 2001), Reimers, *Chem. Rev.* 2007, 107, 590-600, Zosic, *Handbook of electrochemistry* (Elsevier, 2007)). Working with nanoscale electrodes, however, is significantly more challenging, as fabrication is typically labour-intensive, insufficiently reproducible, and the currents obtained from such structures are typically difficult to measure accurately.

The use of nanowire electrodes for ultrasensitive nucleic acids and protein detection has been investigated (Gasparac et al. *J Am Chem Soc* 726:12270). The use of this electrode platform enables the electrochemical detection of picomolar levels of analytes, a level of sensitivity that is not possible using macroscale materials. Although it has been reported that nanowires are able to detect attomolar levels of analytes, this actually corresponds to picomolar levels when dealing with the volumes typically used for analysis. It has also been demonstrated that nanoparticle-modified electrodes may exhibit several advantages over conventional macroelectrodes such as enhancement of mass transport, catalysis, high effective surface area and control over electrode microenvironment (Katz et al. *Electroanalysis* 2004, 16, 19-44, Welch et al. *Anal. Bioanal. Chem.* 2006, 384, 601-619). Manufacturing arrays of nanowire electrodes, however, is non-trivial.

Boron doped diamond microelectrodes modified by electrodeposition of platinum nanoparticles have been used for the oxidative determination of As(III) at levels below 1 ppb (Hrapovic et al. *Anal. Chem.* 2007, 79, 500-507). However, this type of electrode cannot be incorporated into an array-based format for multiplexed experiments.

The analysis of panels of nucleic acid or protein biomarkers offers valuable diagnostic and prognostic information for clinical decision making. Existing methods that offer the specificity and sensitivity to profile clinical samples are typically costly, slow and serial. There is thus a need for an ultrasensitive device for detecting biomarkers in a multiplexed fashion.

SUMMARY OF THE INVENTION

In one aspect, the invention features nanostructured microelectrodes (NMEs). NMEs are electrodes, which are nanotextured and thus have an increased surface area. Preferred NMEs are comprised of a noble metal, (e.g. gold, platinum, palladium, silver, osmium, indium, rhodium, ruthenium); alloys of noble metals (e.g. gold-palladium, silver-platinum, etc.); conducting polymers (e.g. polypyrole (PPY)); non-noble metals (e.g. copper, nickel, aluminum, tin, titanium, indium, tungsten, platinum); metal oxides (e.g. zinc oxide, tin oxide, nickel oxide, indium tin oxide, titanium oxide, nitrogen-doped titanium oxide (TiOxNy); metal silicides (nickel silicide, platinum silicide); metal nitrides (titanium nitride (TiN), tungsten nitride (WN) or tantalum nitride (TaN)), carbon (nanotubes, fibers, graphene and amorphous) or combinations of any of the above. NMEs of the above-described materials are highly conductive and form strong bonds with probes (e.g. nucleic acids and peptides). Preferred NMEs have a height in the range of about 0.5 to about 100 microns (pm), for example in the range of about 5 to about 20 microns (e.g. 10 microns); a diameter in the range of about 1 to about 10 microns; and have nanoscale morphology (e.g. are nano structured on a length scale of about 1 to about 300 nanometers and more preferably in the range of about 10 to about 20 nanometers). NMEs can be any of a variety of shapes, including hemispherical, irregular (e.g. spiky), cyclical (wire-like) or fractal (e.g. dendritic). The surface of an NME may be further coated with a material, which maintains the electrode's high conductivity, but facilitates binding with a probe. For example, nitrogen containing NMEs (e.g. TiN, WN or TaN) can bind with an amine functional group of the probe. Similarly, silicon/silica chemistry as part of the NME can bind with a silane or siloxane group on the probe.

In another aspect, the invention features an NME associated with a probe. In one embodiment, the probe is a nucleic acid (e.g. a ribonucleic acid (RNA), deoxyribonucleic acid (DNA) or analog thereof, including, for example, a peptide nucleic acid (PNA), which contains a backbone comprised of N-(2-aminoethyl)-glycine units linked by peptides rather than deoxyribose or ribose, peptide nucleic acids, locked nucleic acids, or phosphorodiamidate morpholino oligomers. Under appropriate conditions, the probe can hybridize to a complementary nucleic acid to provide an indication of the presence of the nucleic acid in the sample. In another embodiment, the probe is a peptide or protein (e.g. antibody) that is able to bind to or otherwise interact with a biomarker target (e.g. receptor or ligand) to provide an indication of the presence of the ligand or receptor in the sample. The probe may include a functional group (e.g., thiol, dithiol, amine, carboxylic acid) that facilitates binding with an NME. Probes may also contain other features, such as longitudinal spacers, double-stranded and/or single-stranded regions, polyT linkers, double stranded duplexes as rigid linkers and PEG spacers.

In a further aspect, the invention features a plurality of NMEs arrayed on a substrate. Preferred substrates are comprised of a semiconductor material, such as silicon, silica, quartz, germanium, gallium arsenide, silicon carbide and indium compounds (e.g. indium arsenide, indium, antimonide and indium phosphide), selenium sulfide, ceramic, glass, plastic, polycarbonate or other polymer or combinations of any of the above. Substrates may optionally include a passivation layer, which is comprised of a material, which offers high resistance and maintains a small active surface area. Examples of appropriate materials include: silicon dioxide, silicon nitride, nitrogen doped silicon oxide (SiOxNy) or paralyene. In certain embodiments, the plurality of NMEs arrayed on the substrate include probes in conjunction with monolayer spacers, which minimize probe density, thereby maximizing complexation efficiency. Preferred monolayer spacers have an affinity to metal and can be comprised, for example, of a thiol alcohol, such as mercaptohexanol, alkanethiols, cysteine, cystamine, thiol-amines, aromatic thiols (e.g. benzene thiol, dithiol), phosphonic acids or phosphinic acids.

Another aspect features biosensing devices, such as integrated circuits, comprising, for example, a substrate; an electrically conductive lead on the substrate; an insulating or passivation layer covering the lead, the insulating layer having an aperture exposing a portion of the lead; and a nanostructured microelectrode in electrical communication with the exposed portion of the lead, the microelectrode being adapted to generate a charge in response to a biomolecular stimulus (e.g. nucleic acid hybridization or protein-to-protein binding.

In still another aspect, the invention features methods for manufacturing NMEs. The use of electrodeposition to grow nano structured microelectrodes from an NME seed allows the sizes and morphologies of these structures to be finely controlled, and versatile fabrication of electrodes composed of one or a variety of substances. NMEs may be prepared on a biosensing device, such as a chip-based format, such that a series of NMEs may be made on a single chip to enable multiplexed experiments. This NME system may be particularly useful and versatile, allowing adjusting of several parameters, including: the microscale control of the NME size and shape, the nanoscale control of NME nanotexturing, and selection of the NME material.

Yet another aspect features methods for manufacturing biosensing devices having nanostructured microelectrodes. For example, the methods can comprise the steps of providing a substrate and an electrically conductive lead on the substrate, the lead being covered by an insulating layer; etching an aperture in the insulating layer to expose a portion of the lead; and electrodepositing an electrically conductive material on the exposed portion of the lead to form a nano structured microelectrode as described above.

In another aspect, there is provided a biosensing cartridge comprising: a sample chamber for containing a biological sample; a biosensing chamber for containing a biosensing device as described above and carrying out a biosensing process.

In yet another aspect, there is provided a biosensing workstation comprising: a cartridge holder for holding a biosensing cartridge as described above; an instrument tip for accessing the biosensing cartridge; a selection mechanism for selecting a biosensing process to be carried out; a processor adapted to carry out the biosensing process using the biosensing cartridge and to determine results of the biosensing process from electronic signals generated from the biosensing cartridge; and a display for displaying the results of the biosensing process.

A further aspect features methods for carrying out a biosensing process using probe containing nanostructured microelectrodes incorporated into a device as described above; biasing the microelectrode relative to a reference electrode; measuring a reference charge or reference current flow between the microelectrode and the reference electrode; exposing the microelectrode to a biomolecular stimulus (e.g hybridization between a nucleic acid probe with a complementary nucleic acid or binding between a peptide probe and a binding partner present in a biological sample); measuring a charge or current flow generated at the microelectrode in response to the biomolecular stimulus; and determining the amount of biomolecular stimulus present by comparing the measured charge or measured current flow against the reference charge or reference current flow.

NMEs are versatile, robust and easy to work with. In addition, they can be manufactured using existing silicon CMOS foundry fabrication procedures for top-metal fabrication, or simple extrapolations thereof, such as electroless deposition or electrodeposition onto top-metal layers from a CMOS foundry, allowing the manufacture of NMEs to be easily integrated into existing manufacturing facilities. In addition, NMEs are able to consistently attach to probe molecules. Further, NMEs promote ready accessibility of target molecules such that, when a target molecule that is complementary to the NME-attached probe molecule enters into proximity with that probe, hybridization or protein-to-protein binding occurs with high probability. NMEs are further compatible with the performance of electrocatalytic electrochemistry employed in the read-out of the hybridization event.

Other features and advantages of the inventions disclosed herein will become apparent from the following detailed description and claims.

DETAILED DESCRIPTION OF THE INVENTION

The present disclosure describes nanostructured microelectrodes (NMEs), which may be used in a biosensing device, such as a biosensing chip.

NMEs

Figure 1A:
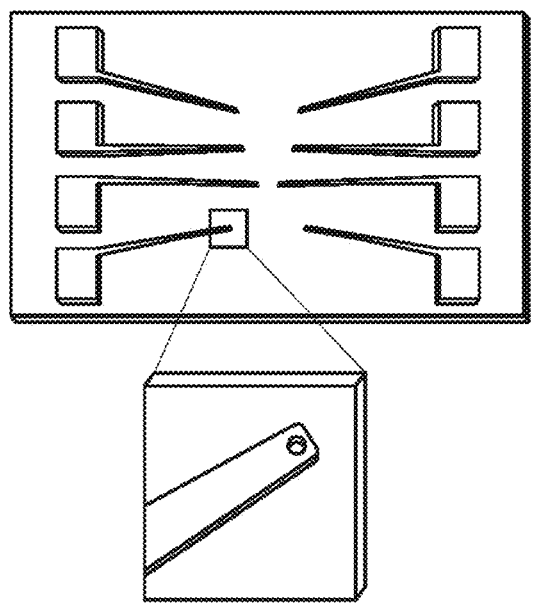
FIG. 1(A) is a schematic of an NME biosensing device.

FIG. 1A shows a schematic diagram of an exemplary device incorporating NMEs. In the example shown, the device is a chip having an array of eight leads. In this example, the NME is formed on gold leads that taper to a width of 5 microns. The lead is provided on a substrate of Si and $SiO_2$, although other suitable substrate materials may be used. On top of the lead, an insulating layer, such as $SiO_2$, is deposited to electrically insulate and passivate the lead. An aperture, in this case a 500 nm hole, is created in the insulating layer to expose a portion of the lead.

Figure 1B:
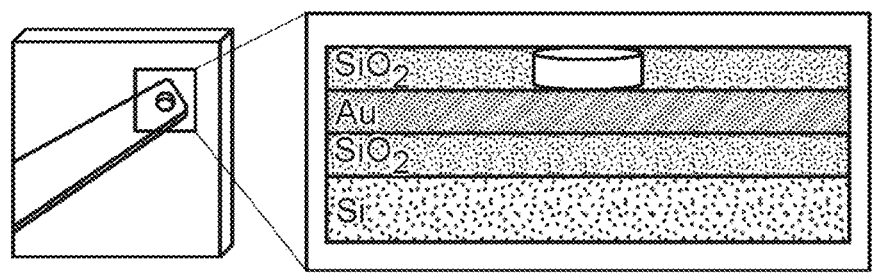
FIG. 1(B) is a schematic cross-sectional view of an aperture for forming an NME.

FIG. 1B is a side view of the portion of the chip where the aperture is located, showing the layers of the device. Most commonly known photolithography techniques may be suitable for creating an aperture, such as 100 nm to 1 μm diameter apertures. This is typically achievable in existing fabrication facilities with high robustness and reproducibility. Given that only this exposed surface is electrochemically active, electrodeposition (Menke et al. *Nature Mater.* 2006, 5, 914-919) may be used to grow an NME within this space.

Figure 1C:
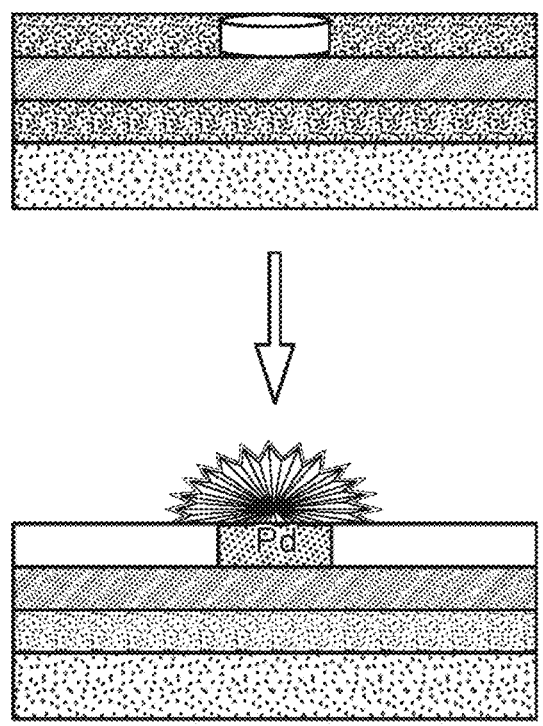
FIG. 1(C) is a schematic view of the formation of an NME in an aperture.

FIG. 1C is a cross-sectional schematic of an example of NME deposition, using Pd for the NME. This process will be described in greater detail below.

Figure 2A:
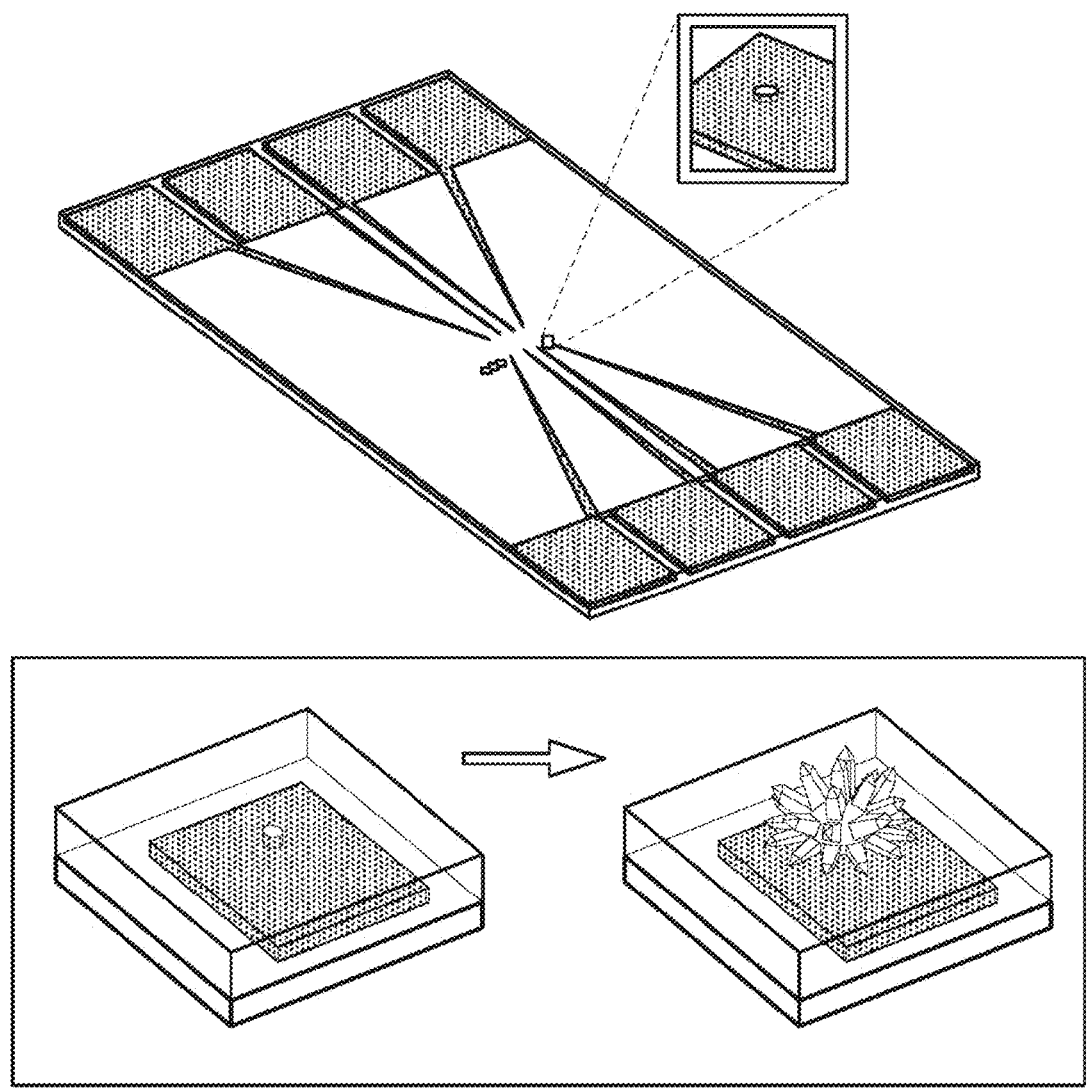
FIG. 2(A) is a schematic of an NME biosensing device.
Figure 2B:
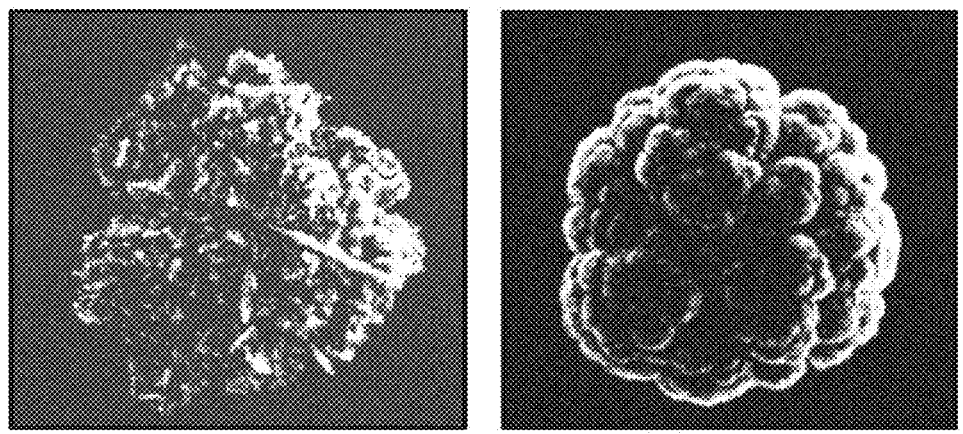
FIG. 2(B) shows SEM images of NMEs.

Reference is now made to FIG. 2, which also illustrates the formation of an NME on a chip. As in FIG. 1A, small electrodes are provided in situ on a chip, with the position and electrical contacting of the NMEs defined photolithographically. As in FIG. 1, this chip is an 8-fold multiplexed passive chip. On a silicon substrate, a ~350 nm thick gold layer is patterned, using conventional photolithography techniques, to connect eight 5-μm-wide Au leads to large metal pads for connection to off-chip instrumentation. A pinhole-free insulating $SiO_2$ layer is deposited and patterned to create ~500 nm openings (e.g., by etching) at the end of each of the Au leads, to expose a section of the lead. A metal NME is then plated in this opening using electrodeposition.

The NME may comprise different conductive materials. Some examples of NMEs have been formed as follows, although variations are possible and will be described in greater detail below: Branched fractal Pd NMEs were deposited in an aqueous solution containing 5 mM of $H_2PdCl_4$ and 0.5 M of $HClO_4$ using DC potential amperometry at −250 mV for 15 s. Hemispherical Pd NMEs with nanoscale roughness were deposited in an aqueous solution containing 5 mM of $H_2PdCl_4$ and 0.5 M of HCl using DC potential amperometry at −100 mV for 300 s. Smooth hemispherical Pd NMEs were fabricated in the same solution at 0 mV for 300 s. Au NMEs were fabricated in a gold bath containing 0.01 M solution of $HAuCl_4$ and 0.5 M $H_2SO_4$ at −100 mV for 40 seconds. Pt NMEs were fabricated in a platinum bath containing 5 mM solution of $H_2PtCl_6$ and 0.5 M $H_2SO_4$ at −100 mV for 500 s. NME size and morphology can be controlled by varying the metal salt concentration, type and concentration of the supporting electrolyte, and electrodeposition potential and duration.

Figure 3:
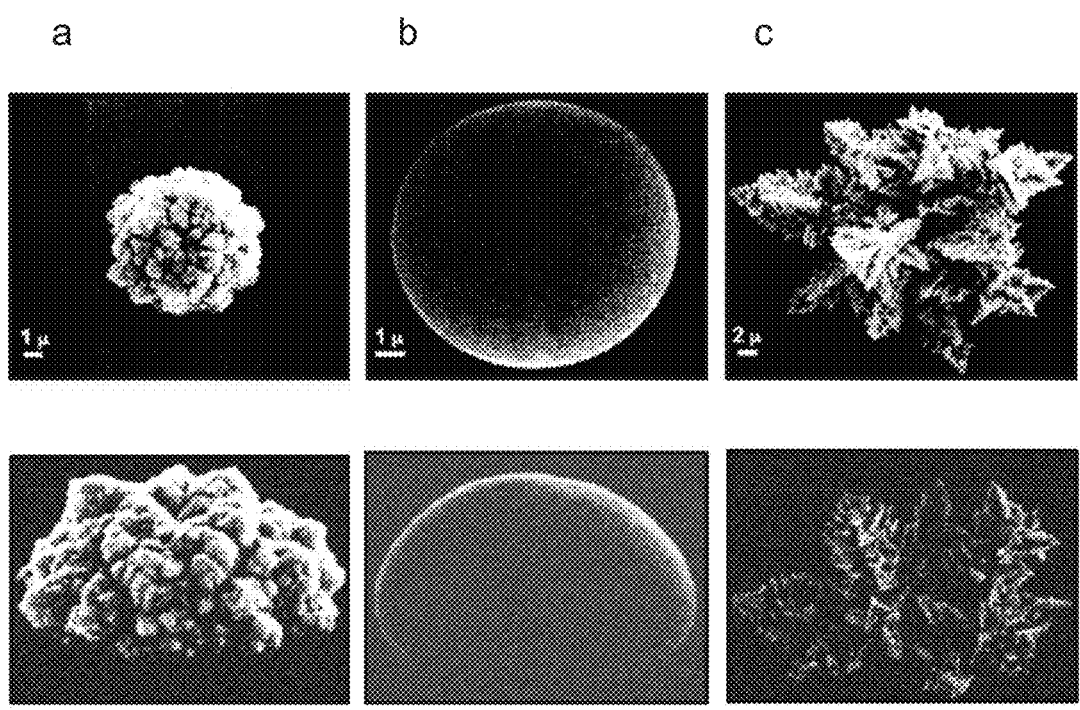
FIG. 3 is a schematic of an NME with probes, further showing the presence of spacers in the probe monolayer and between the electrode and the probe.

FIG. 3 is a schematic of an NME with probes with spacers in the probe monolayer and between the electrode and probe. A chemical solution containing a metal cation can be brought into communication with the surface of the NME and a reference electrode. The reference electrode may be an NME or a conventional electrode on same lead. An electrical bias can be provided between the NME and the reference electrode. The chemical solution can then be removed and the electrodes washed. A solution containing the probe molecule can then be brought into communication with the surface of the NME. The probe molecule may be modified or functionalized so that it binds to the surface of the NME. For example, the probe molecule may be functionalized with a thiol, amine, or carboxylate group.

Figure 4:
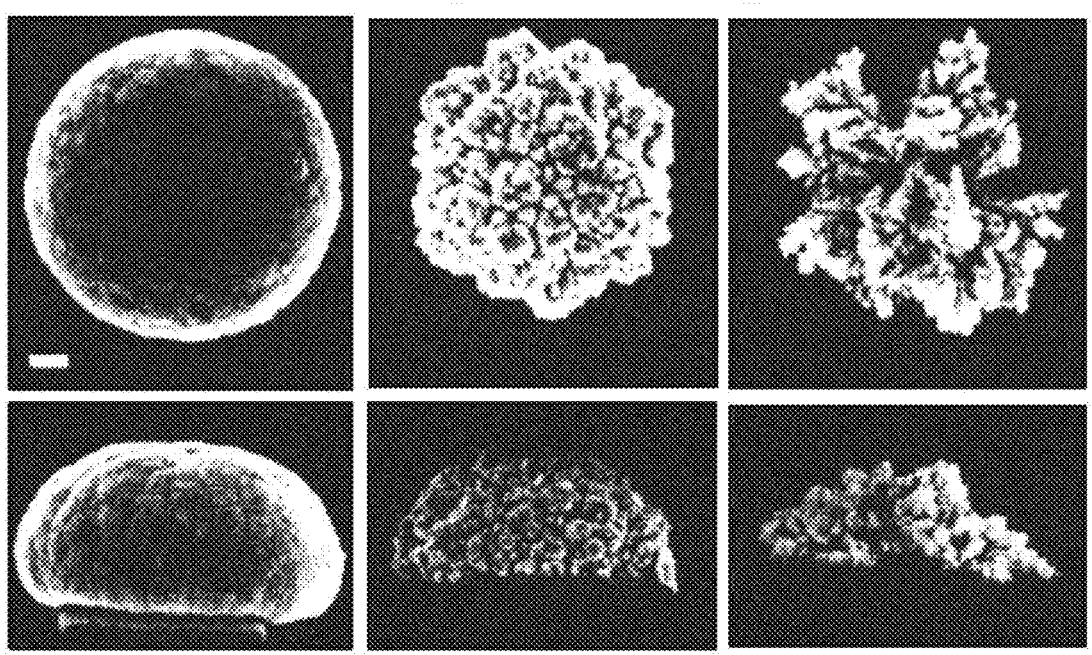
FIG. 4 are SEM images of NMEs with increasing degrees of nanostructuring.

NMEs with increasing nanostructuring are shown in FIG. 4. Unexpectedly, variation of electrodeposition conditions allowed growth of extremely smooth hemispherical microelectrodes (left); highly branched nanoscale fractal structures (right); or hemispheres with nanoscale roughness (center). The structure on the left was made with HCl as a supporting electrolyte with an applied potential of 0 mV. The center structures were also made with HCl as a supporting electrolyte but with an applied potential of −100 mV. The structure on the right was made with $HClO_4$ as a supporting electrolyte and an applied potential of −250 mV. The scale bar on the figure corresponds to 5 μm unless otherwise indicated.

Figure 5A:
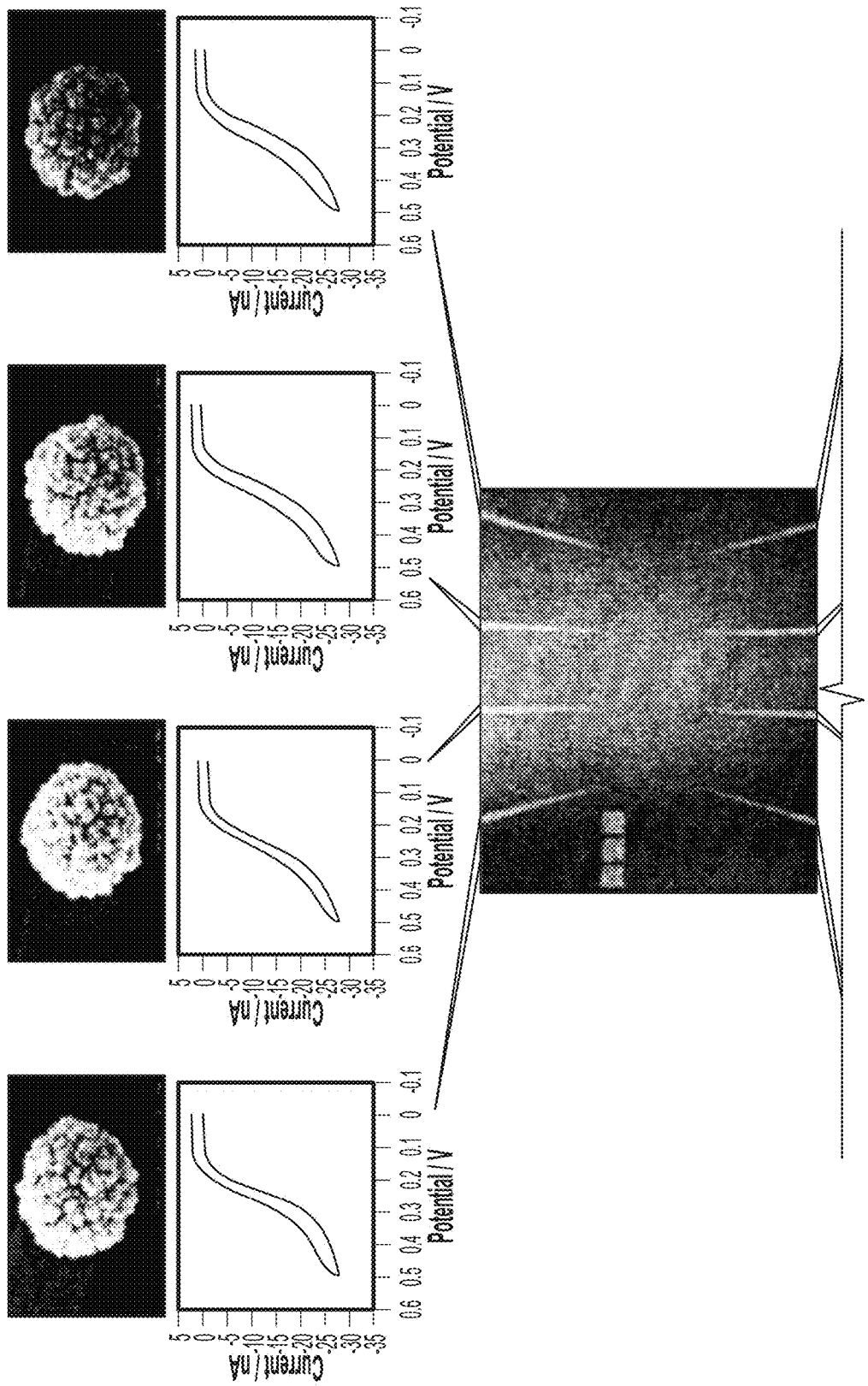
FIGS. 5A and 5B illustrate steps involved in the sensing of specific sequences using an NME.
Figure 5B:
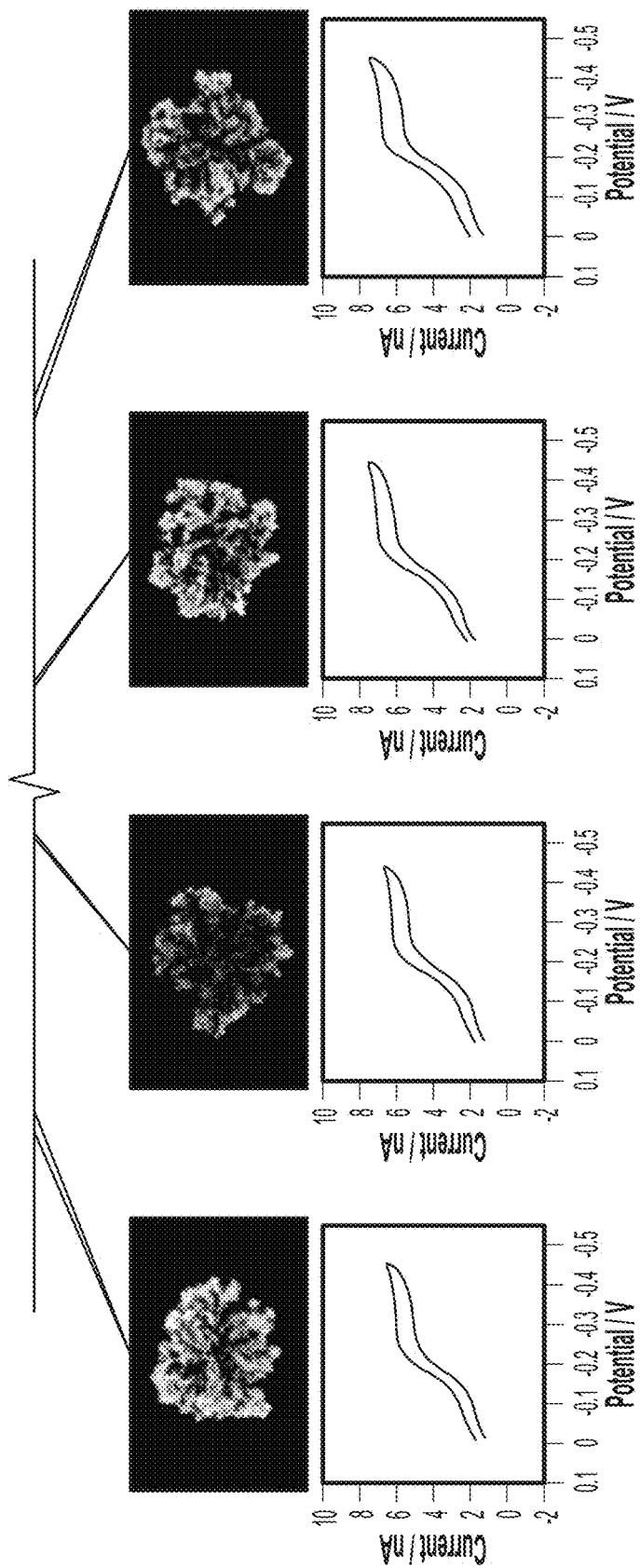

FIGS. 5A and 5B illustrate steps involved in the sensing of specific sequences (Lapierre et al., *Anal. Chem.* 75:6321, Ratilainen et al., *Biochemistry* 39:7781, Tomlins et al., *Science* 310:644) In this example, Pd NMEs are first modified with thiol-derivatized probe sequences, and then target sequences are hybridized. The presence of the target is then transduced using an electrocatalytic reporter system. Electrocatalysis provides electronic amplification, or gain, facilitating high-sensitivity readout: hundreds of electrons may result from each biomolecular complexation event. The approach used herein relies on the primary electron acceptor $Ru(NH_3)_6{}^{3+}$, which is electrostatically attracted to the electrode surfaces at levels that are correlated with the amount of bound nucleic acid. The inclusion of $Fe(CN)_6{}^{3-}$ during electrochemical readout serves to regenerate the Ru(III) substrate, as the Fe(III) species is even easier to reduce, but it is electrostatically repelled from the electrode and thus only undergoes chemical reduction by Ru(II). This method is also label-free and does not require the sample to be processed in any way.

The biosensing device may be provided in the form of a chip, such as an integrated circuit (IC) chip. In general, an IC incorporating the NME may have a substrate with an electrically conductive lead that is covered by an insulating layer. The insulating layer has an aperture that exposes a portion of the lead, and the NME is provided at the exposed portion of the lead. The NME is responsive to a biomolecular stimulus. In particular, the NME may be functionalized with probe molecules that undergo a hybridization reaction with a target biomolecule (e.g., a nucleic acid sequence), resulting in a charge generated at the NME. The IC also has a charge storage (e.g., a capacitor or a battery) in electrical communication with the lead to store this generated charge. In typical usage, the NME may be exposed to a sample for a known time duration or an integration period, and the charge stored over that time would then be indicative of the presence and/or amount of the target biomolecule.

The stored charge may be communicated to a computing device for analysis, or may be displayed (e.g., through a digital display component) for direct reading of the charge stored after the integration period.

Such an IC may be manufactured using common IC manufacturing equipment, allowing this device to be easily manufactured and to be less costly than other forms of biosensing microelectrodes. The materials used may be those already commonly used in IC manufacturing. For example, the substrate may be made from silicon, quartz, glass, ceramics, silica, sapphire, gallium arsenide, or other materials currently used for ICs. The substrates or supports can incorporate conductive material to serve as an electrode. Conductive supports with a gold surface may also be used. The supports usually comprise a flat (planar) surface, or at least a structure in which the probes or p to be interrogated are in approximately the same plane. The support can be an electrode, or can be attached to an electrode.

The lead may be made of Au, Al, W, TiN, polysilicon or other commonly used lead materials. The IC may include a transistor, such as a field-effect transistor (FET) including n-type silicon channel FETs and p-type silicon channel FETs, or a bipolar transistor including n-p-n bipolar junction transistors and p-n-p bipolar junction transistors.

The IC may be provided with, immersed in or otherwise exposed to an electrocatalytic solution in chemical and electrical communication with the NME. This may assist in charge generation in the NME.

Figure 6:
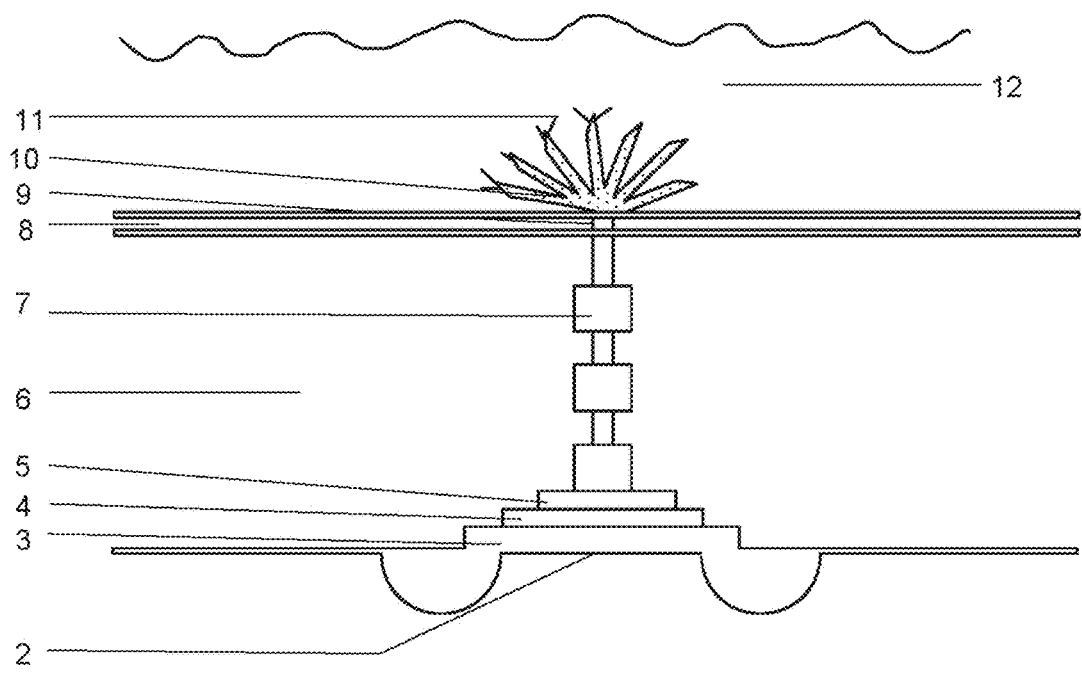
FIG. 6 is a cross-sectional view of an integrated circuit having an NME.

Reference is now made to FIG. 6. This figure shows a cross-section of an integrated circuit suited to sensing the presence of biomolecules in a biological sample. The substrate (1) is a conventional semiconductor device substrate such as silicon. The channel of a transistor (2), a gate oxide (3), and a polysilicon gate electrode (4) are shown to illustrate the use of conventional CMOS electronics to form the integrated circuit's transistors. A metal (5) is used to contact the gate electrode. A passivation oxide (6) separates the silicon transistor levels below from the top surface of the chip above. A series of metal vials (7) and interconnects provide selective paths for electrical communication between the transistor layer and the top electrode(s). A substantially planar top surface is a heterogeneous combination of top electrodes (9) and top insulating material (8). The figure illustrates an NME (10) provided on the electrode, for example using the methods described above. The figure illustrates probe biomolecules (11) such as thiol-terminated nucleic acids that are displayed for efficient hybridization with complementary target molecules. An electrocatalytic solution (12) may be employed to provide catalytic read-out of hybridization with the biomolecules (11). Electrical potentials are conveyed, and currents flowed, in a continuous fashion from the NME (10) through the electrical contacts (9) (7) (5) (4) down to the electronic circuitry that resides beneath.

Figure 7:
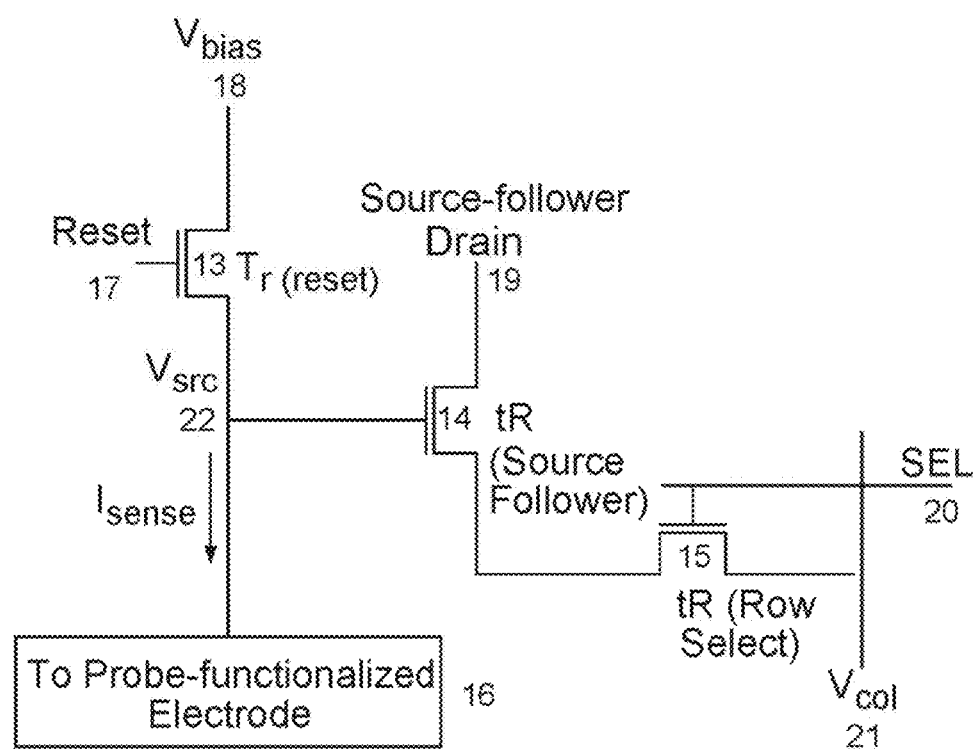
FIG. 7 is a circuit diagram of a circuit that may be used with an NME.

Reference is now made to FIG. 7, showing a circuit diagram of an example circuit that may be used with the disclosed NME. In this example, the circuit may provide the following functions: biasing of the probe-functionalized NME; integration of the current flowing through the NME into a charge store having a known charge-storage capacity; read-out of the voltage on the charge-store; and selection of the charge-store or NME of interest when a two-dimensional array of stores and electrodes is provided in the context of a highly multiplexed array chip.

The components of the example circuit are now described. A bias voltage is provided at $V_{bias}$; atypical choice of bias may be in the range of about 0.1-2.8 V. A bias voltage $V_{bias}D$ is provided at the source-follower drain; a typical choice may be in the range of about 0.1-2.8 V. A bias voltage $V_{bias}R$ is provided at the reset node; a typical choice may be an adjustable value between about −2 V and 2.8 V. The signal voltages are $V_{src}$ which may typically be in the range of about 1.5-2.5 V. The column voltage $V_{col}$ may be in the range of about 1.5 V-0.5 V. Timing control signals include that for row select (e.g., range may be about 0-2.8 V) and for reset (e.g., range may be about 0-4 V). The transistors may be the reset transistor Tr(Reset), the read-out buffer transistor TR(source-follower), and the row-select transistor TR(row-select).

The above biases, signal voltages and timing control signals are examples only and other values may be used. These biases, voltages and signals may be selected or adjusted to suit certain applications or manufacturing conditions, as is commonly known in the art. In this example, the probe-functionalized NME may include a NME functionalized using a thiolated nucleic acid probe, for example a probe as described above. $V_{src}$ is applied to the probe-functionalized electrode and $V_{bias}R$ is applied to a second electrode, which may be a NME or any other common electrode, in electrical communication with the electrocatalytic solution. This results in voltage difference between the probe-functionalized electrode and the electrocatalytic solution. A current may thus flow as a consequence of this potential difference. The amount of current flowing may be typically dependent on the amount of hybridization on the probe-functionalized NME, that is the current may be indicative of the amount of target thus detected by the NME.

The operation of the example circuit is now described. In order to capture the current flowing, $I_{sense}$, the reset transistor is turned on by setting the node 'reset' high enough (e.g., up to 4V, which may be through an on-chip charge-pump or regulator circuit as commonly known in the art) so that node 22 will be charged to a voltage equal to $V_{bias}$ (node 18) which may be typically set to the supply rail: e.g., 2.8V. This is the reset phase. Once this 'reset' operation is completed, Node 17 may be set to 0V to turn off the reset transistor Tr(Reset) (13). In doing so, charge injection and parasitic capacitive feedthrough effects will cause node 22, now becoming a floating node, to drop by approximately 300 mV. Therefore after the 'reset' operation the actual 'reset' voltage value at node 22 is approximately 2.5V. At this time, the current $I_{sense}$ flowing is dependent on the voltage applied (i.e., $V_{src}-V_{bias}R$). With $V_{bias}R$ being able to be set arbitrarily to any voltage level from −2V to 2.8V, the applied potential difference may be adjusted. The current $I_{sense}$ discharges the parasitic capacitance at the $V_{src}$ node (22) and its voltage level drops at a rate dependent on the value of the parasitic capacitance at $V_{src}$ (node 22) as well as the flowing $I_{sense}$ during the integration time. After a specific integration time, the resulting integrated voltage at node 22 will be read out through transistors TR(source-follower) and TR(row-select), the source follower buffer transistor and the row-select transistor, by setting the node SEL (20) to a high level (2.8V).

The charge store that is discharged at node 22 may comprise parasitic capacitance of one or more of the transistors that are in electrical communication with the electrode of the pixel region at $V_{src}$ (node 22). The electrode at $V_{src}$ (node 22) may be in electrical communication with the gate of a transistor, such as Tr(source-follower) 14, which provides a parasitic capacitance. In one example embodiment, the charge store may be provided at least in part by a parasitic capacitance between the gate and drain of the source follower transistor, Tr(source-follower) 14, and a parasitic capacitance between the source and substrate of the reset transistor, Tr(Reset) 13. These are parasitic capacitances between the structures on the semiconductor substrate (e.g., the poly, n-well and substrate) on which or in which the pixel circuit is formed. In an example embodiment, these parasitic capacitances may be in the range of about 1-2 femtoFarads or more generally in the range of about 0.5 to 3 femtoFarads or any range subsumed therein. The contacts to the probe-functionalized NME may be formed in different layers above the regions of the semiconductor substrate used to form the transistors. In an alternate embodiment, the polarity of the bias may be reversed and the parasitic capacitance at $V_{src}$ may be charged instead of discharged during the integration period.

Figure 8:
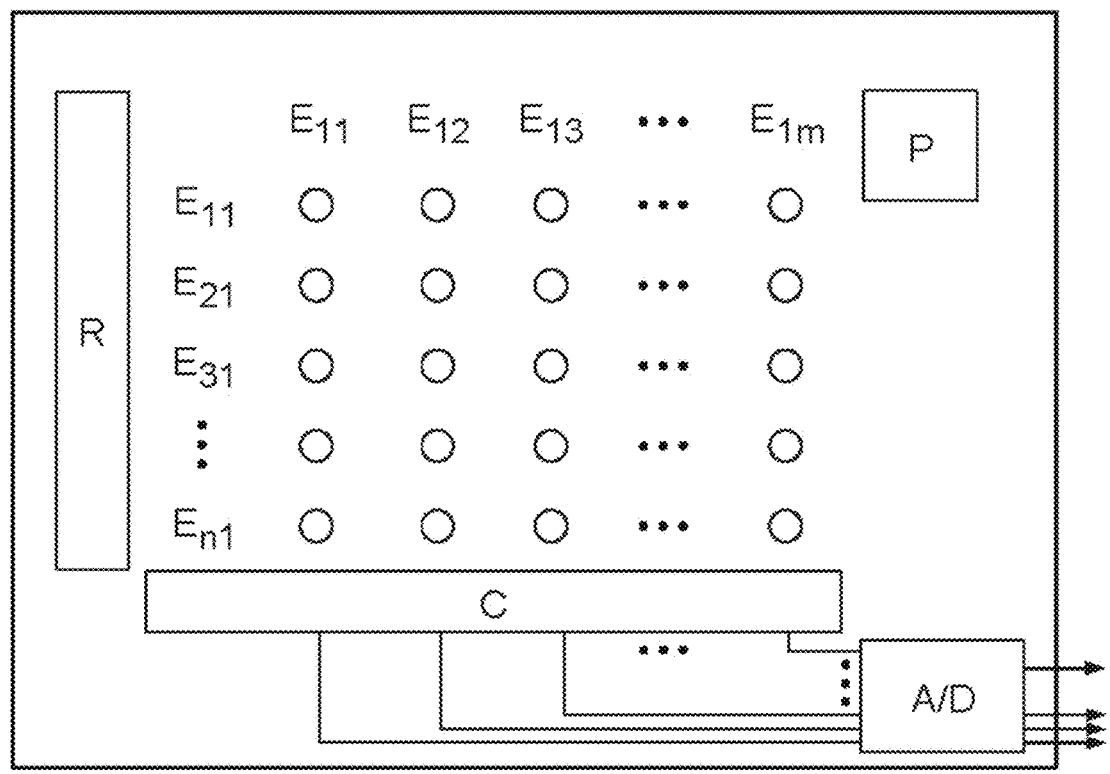
FIG. 8 is an illustration of a biosensing device having an array of NMEs.

Reference is now made to FIG. 8, which shows a top view of an example IC that has a multiplexed array of individually-addressable probe-functionalized NMEs. By individually addressable, it is meant that each NME may be individually electrically accessed, such that the current or charge generated by each NME may be individually measured. In this example, the NMEs are arrayed in a row-column fashion. There are n rows and m columns for a total of m×n independent NMEs. If there were only a single row or column of NME, then it may not be necessary to have row/column address circuitry. However, when large total numbers of NMEs are desired on a single device, it may be more efficient to array them in a two-dimensional grid or similar, and thus independent electrical access to each NME may be useful. This may be efficiently achieved using the circuitry illustrated in FIG. 7. In this approach, the charge associated with the current flowing through each NME is integrated into a charge storage, such as a capacitor; and a voltage proportional to the stored charge may be read out for the NME in a particular row by setting the node SEL (20) to a high level and monitoring the voltage on that column $V_{col}$.

The figure illustrates that, for each column, there may exist a time-dependent signal (whose time-dependence may be determined by the clocking of the row-address circuitry) which, in some embodiments, may be fed, in cases with the aid of electronic buffering or amplification, into an analog-to-digital converter. The analog-to-digital converter may accept signals having a pre-determined voltage swing (such as 0-1 V, typically) and, for each input channel, may carry out a quantization operation in which a digital representation of the analog level in that signal is estimated. The output of the A/D converter is a digital stream which combines parallelism (e.g., multiple parallel wires, each corresponding to a significant figure in the binary representation of the values) and serial timing (e.g., a timed representation of sequential data elements corresponding, for example, to different probe-functionalized NMEs).

Figure 9:
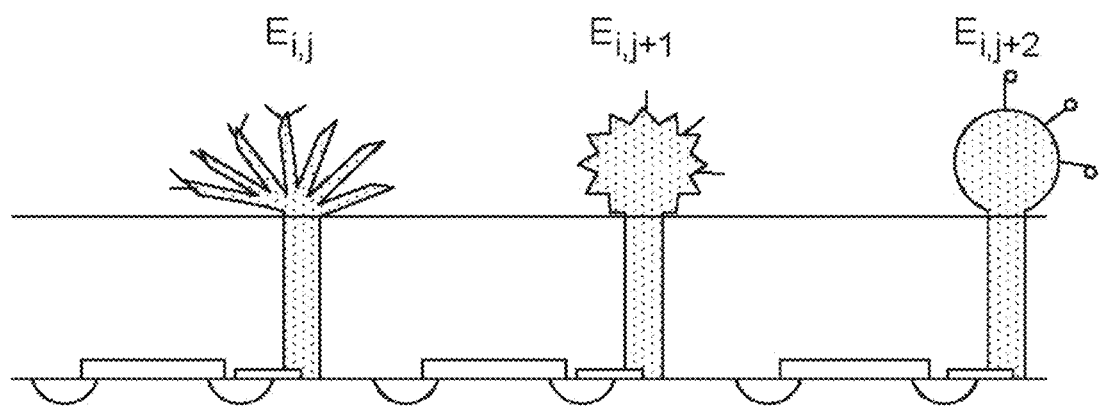
FIG. 9 is an illustration of a biosensing device having different NMEs.

Reference is now made to FIG. 9, showing three adjacent NMEs along a single row, in a configuration that may be provided on a biosensing device or IC as described above. These three NMEs are read using three different columns j, j+1, and j+2. This figure illustrates a number of features with respect to the differences among NMEs.

NMEs $E_{i,j}$ and $E_{i,j+1}$ may be functionalized both with the same class of probes (e.g. thiolfunctionalized PNA), but the sequences may be different. That is, each NME may be functionalized with similar probes that have different target biomolecules. In this example, electrodes $E_{i,j}$ and $E_{i,j+1}$ are response to different sequences present in the sample under study. In sum, the use of different fimctionalizations enables sensing of biomolecules within a single class, but having a different sequence, conformation, or functionality.

NMEs $E_{i,j}$, $E_{i,j+1}$, and $E_{i,j+2}$ are shown having different morphologies and/or sizes, and different degrees of nanostructuring. As discussed above, different morphologies and/or sizes may provide both different limits of detection, and different dynamic ranges, in detecting of target molecules. By incorporating NMEs having different morphologies and/or degrees of nano structuring onto one device, it may be possible to expand the dynamic range of target concentrations that may be sensed using a single device. In sum, the use of different NME morphologies, sizes and/or nanostructurings may enable sensing of a wider range of concentrations of a given target species than would otherwise be achieved if only one morphology/nanostructuring were provided on a biosensing device.

NMEs $E_{i,j+1}$ and $E_{i,j+2}$ are also depicted as being functionalized using different classes of probe molecules. For example, $E_{i,j+1}$ may be functionalized using a nucleic acid such as PNA, and $E_{i,j+2}$ may be functionalized using antibodies which attach to the electrode. In sum, the use of different classes of probe molecules may enable sensing of different classes of target biomolecules, for example ranging from DNA to RNA to micro-RNA to proteins, using a single biosensing device.

Biosensing Cartridge and Workstation

The biosensing device as described above may be incorporated into a biosensing cartridge. Such a cartridge may contain chambers for sample processing such as disruption and resin or bead-based nucleic acid purification, as well as a chamber for the biosensing device. The cartridge may be self-contained, for example all necessary reagents may be contained in the lid of the cartridge. The cartridge may be reusable, or may be disposable. A disposable cartridge may minimize the risk of cross-contamination between samples.

The cartridge may be used in a biosensing workstation for coordinating and carrying out the biosensing process. Components of the workstation may include sample holders, instrument tips such as pipettors for manipulation of the sample, a sample identification module, a selection mechanism for selecting a test to be carried out, an electronic display for indicating the results of a biosensing test and a processor for managing these components and carrying out the selected tests. The workstation may hold a number of different cartridges at one time (e.g., ten or more). The workstation may allow random access to the cartridges— that is, independent tests may be run at any time on any cartridge in the workstation. The workstation may have disposable instrument tips, which would be the only part of the workstation that comes into direct contact with the sample and reagents. Disposable tips, together with disposable cartridges, may minimize the risk of cross-contamination between samples tested in the workstation.

In general, a biosensing cartridge may have a first chamber for containing the sample to be tested, and a second chamber containing the biosensing device as described above. There may be addition chambers to perform other actions on the sample, such as purification, and/or subdivision (e.g., through chemical, mechanical or vibrational means). Some processing and disruption of the sample may be carried out in the first chamber itself. The sample may be introduced from the first to the second chamber for detection by the biosensing device in the second chamber. There may be pre-set time interval from activation of the device or start of the test to the introduction of the sample into the second chamber. This time interval may allow the biosensing device to be suitably biased or otherwise readied for the test. The charge or current flow generated in the biosensing device may be measured after an integration period, as described above.

Figure 10:
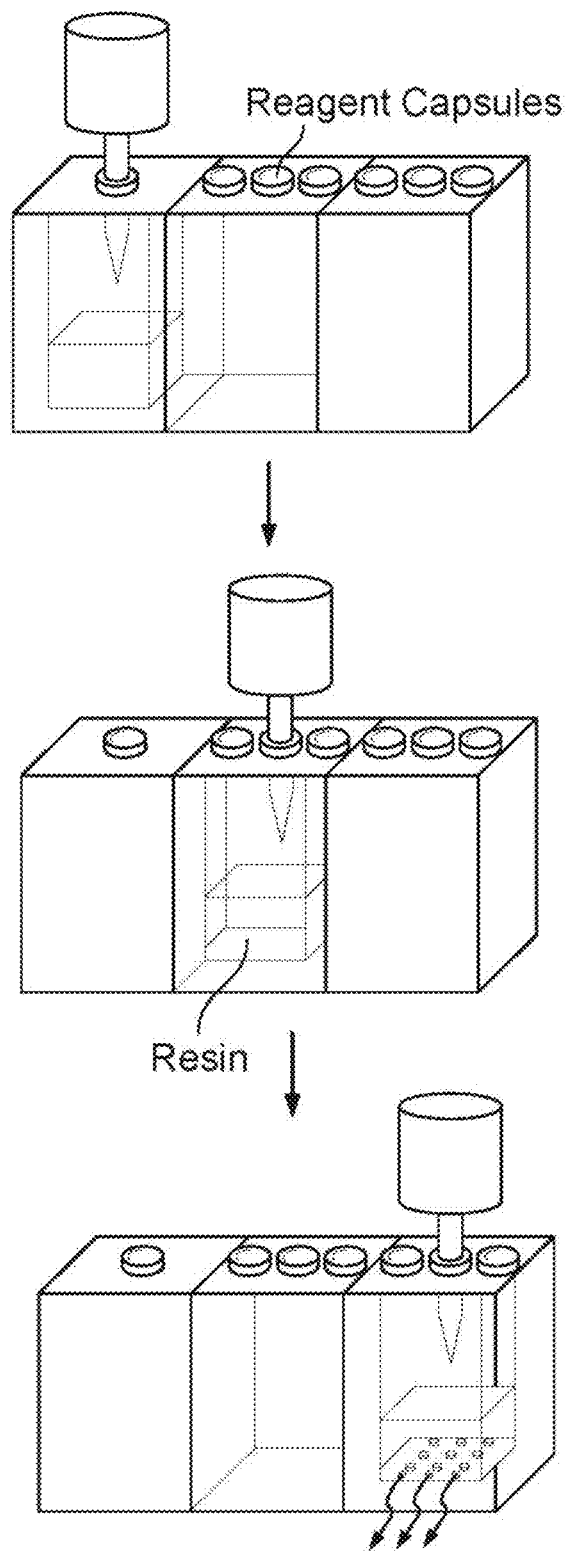
FIG. 10 is a schematic illustration of a biosensing cartridge.

Reference is now made to FIG. 10, showing an example of a biosensing cartridge and the steps of using such a cartridge. In this example, the cartridge has three chambers, a sample chamber containing the sample, a purifying chamber for purifying the sample, and a biosensing for performing the biosensing. As shown in this example, the lid of the cartridge is provided with capsules containing reagents for each chamber, and through which an instrument tip may be inserted. This allows the cartridge to be self-contained, already containing the reagents suitable to carry out the biosensing operation and tailored to the particular probes and/or target biomolecules of the biosensing device being used. In this example, the sample chamber has one capsule, for accessing the sample. The purifying chamber has three capsules—two containing a washing reagent, and one containing an elution buffer. The biosensing chamber has three capsules—each containing an electrochemical mix containing analytes for the biosensing device. The instrument tip may be inserted sequentially in each capsule, in order to carry out the biosensing operation. For example, the capsule on the sample chamber may contain a lysis buffer containing chemical dénaturants (e.g., urea or formamide); the capsules one the purifying chamber may have two capsules containing a wash buffer and the elution buffer may be a standard buffer, such as one containing low levels of sodium, chloride and tris salt; the capsules on the biosensing chamber may contain redox reporter groups such as ruthenium hexamine, ferricyanide and a buffer containing sodium, phosphate, chloride and magnesium.

In use, the sample is first extracted from the sample chamber through its single capsule. The sample is then introduced into the purifying chamber, where it is washed twice as the instrument tip is introduced through the two washing capsules and the elution buffer is introduced. Through this process, the sample may be prepared for biosensing by the biosensing device. For example, in the case of a nucleic acid sample, the process in the purifying chamber may isolate the RNA or DNA in the sample. The purified sample is then introduced into the biosensing chamber, through each electrochemical capsule. The biosensing device in the biosensing chamber may then detect any target biomolecules present in the sample, and the generated current or charge may be measured. Where the cartridge is used in a workstation, the processor in the workstation may read this generated current or charge and determine the presence of the target biomolecule based on this reading.

Figure 11:
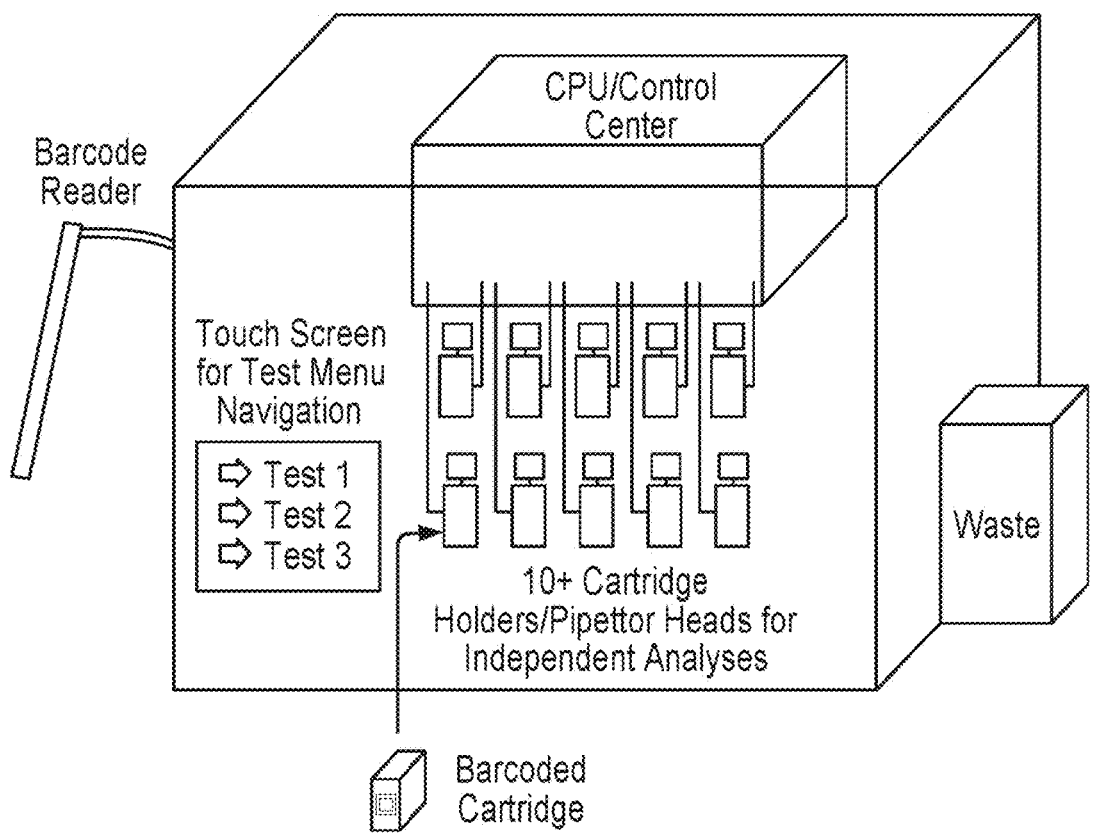
FIG. 11 is a schematic illustration of a biosensing workstation.

Reference is now made to FIG. 11, showing an example of a biosensing workstation. This work station includes a bar code reader, allowing identification of samples using unique bar codes provided on each cartridge. The workstation has a selection mechanism, in this example a touch screen that allows the selection of a particular test to be carried out. There is also a waste container for disposing any wastes generated by the biosensing process. The processor of the workstation may be connected to an external computing device, such as another workstation, for further analysis. This connection may be through a wireless network. The workstation may be relatively small (e.g., a footprint of 1.5×1 ft), allowing convenience and ease of use.

Methods of Use

Methods for using NMEs and devices comprising the same is now described. A device may be provided with the NME already functionalized with a probe molecule, or the probe molecule may be bound to the NME when preparing the device for use. The device is then biased for use, for example by adding an electrocatalytic reporter and waiting a certain time interval. In addition to the NME, there may be a reference electrode, which may or may not be an NME, in contact with the electrocatalytic reporter but not in contact with the sample. The current flow or voltage bias generated over this time interval between the NME and the reference electrode may be measured and recorded as the reference point. The NME is then exposed to a sample of interest, and the current flow or charge generated over a certain time interval (also referred to as the integration period) may be measured. By comparing the difference in current flow or charge between the exposure time interval and the biasing time interval, the concentration, binding and/or amount of target biomolecule in the sample may be determined.

Devices comprising NMEs, as described herein, may be used in conjunction with appropriate probes to detect the presence or absence of particular biomarkers in a sample. A "sample" or "biological sample" as herein refers to any natural (e.g. plant, animal, algal, bacterial or viral) or synthetic material containing DNA, RNA and/or proteins, including, for example, clinical samples, such as tissues, cell cultures or fluids isolated from an individual (including without limitation blood, plasma, serum, cerebrospinal fluid, lymph, tears, urine, saliva, mucus, synovial fluid, cerebrospinal fluid and tissue sections) environment (e.g., water, food or air samples). Biological samples may be further processed via a variety of means, including lysis (electrical, mechanical and chemical), electrophoresis, enzymatic digestion. Most often, the sample has been removed from an organism, but the term "biological sample" can also refer to cells or tissue analyzed in vivo, i.e., without removal.

Typically, a "biological sample" will contain cells, but the term can also refer to non-cellular biological material, such as non-cellular fractions of blood, saliva, or urine. "A biological sample" further refers to a medium, such as a nutrient broth or gel in which an organism has been propagated, which contains cellular components, such as proteins or nucleic acid molecules.

Probes for use with the instant described NMEs may be comprised of nucleic acids. A "nucleic acid probe" refers to a nucleic acid (e.g. a ribonucleic acid (RNA), deoxyribonucleic acid (DNA) or an analog thereof, including, for example, a peptide nucleic acid (PNA), which contains a backbone comprised of N-(2-aminoethyl)-glycine units linked by peptides rather than deoxyribose or ribose linked by phosphodiesterase linkages) capable of binding to a target nucleic acid of complementary sequence through one or more types of chemical bonds, usually through complementary base pairing, usually through hydrogen bond formation. As used herein, a nucleic acid probe may include natural (i.e., A, G, C, or T) or modified on bases (7-deaza-guanosine, inosine, etc.) or on sugar moiety. In addition, the bases in a probe can be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. By assaying for the presence or absence of the probe, one can detect the presence or absence of the select sequence or subsequence. Methods for detecting target nucleic acids using nucleic acid probes are described, for example, in U.S. Pat. No. 7,361, 470 entitled "Electrocatalytic Nucleic Acid Hybridization Detection." and US 2005/0084881 of the same name.

"Hybridization" refers to any process by which a strand of nucleic acid binds with a complementary strand through base pairing. "Hybridization conditions" refer to standard conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety. Non-limiting examples of hybridization conditions include low stringency hybridization conditions, moderate stringency hybridization conditions and high stringency hybridization conditions.

In another embodiment, the probe is a peptide (comprised of, for example, 4-40 amino acids) or proteins (e.g. antibody) that is able to bind to or otherwise interact with a biomarker target (e.g. receptor or ligand) to provide an indication of the presence of the ligand or receptor in the sample. Methods for detecting analytes using peptide or protein probes are described, for example in International patent application WO 2007/094805 (PCT/US2006/013771) entitled "Method for Electrocatalytic Protein Detection."

Probes may include a functional group (e.g., thiol, dithiol, amine, carboxylic acid) that facilitates binding with an NME. Probes may also contain other features, such as longitudinal spacers, double-stranded and/or single-stranded regions, polyT linkers, double stranded duplexes as rigid linkers and PEG spacers.

As described above, the surface nanostructure of the NME may be controlled, and may influence the sensitivity and/or efficiency of a device having the NME. In Example 1, the influence of surface nanostructure on the detection efficiency for nucleic acids was investigated. Two different types of NMEs were compared—a more finely nano structured NME obtained with a low deposition potential was compared to a more coarsely textured one obtained with a higher deposition potential.

While concentrations as low as 1 pM could be detected with the more finely nanostructured NME obtained with a low deposition potential, the detection limit was increased to 10 pM for the more coarsely textured one obtained with a higher deposition potential. These results demonstrate that increased nanostructuring contribute to more sensitive biosensing capabilities in an electrode platform. This analysis revealed that the more finely structured NMEs showed greater responsiveness to sub-nM concentrations of target sequences.

The 10 aM sensitivity observed here with the disclosed NMEs and electrocataytic reporter system provides a low detection limit for a label- and PCR-free sensor; the detection limit corresponds to the detection of <100 copies of the target sequence. While the measurement of 60-1000 copies of target sequence has been achieved previously with electrochemical detectors exploiting multi-step catalytic readout (Munge et al., *Anal. Chem.* 77:4662, Nicewamer-Pena et al., *Science* 294:137, Park et al., *Science* 295:1503, Sinensky et al., *Nat. Nano.* 2:653, Steemers et al., *Nat. Biotechnol.* 18:91, Xiao et al., *J. Am. Chem. Soc.* 129:11896, Zhang et al., *Nat. Nano.* 1:214, Zhang et al., *Anal. Chem.* 76:4093), the disclosed device provides this measurement on a chip-based platform with single-step readout.

Example 2 describes use of a multiplexed electrode platform, as described herein, to directly read a panel of cancer biomarkers in clinically-relevant samples using electronic signals. The system combines nanotextured electrodes with rapid catalytic readout to achieve a long-standing goal: the multiplexed analysis of cancer biomarkers using an inexpensive and practical platform.

Example 3 describes the use of an NME based chip to detect microRNA, one of the most challenging detection targets. Electronic readout of microRNA profiles offers a rapid, yet highly accurate, method to directly assay RNA samples for specific sequences without the need for target amplification.

Although the provided examples are directed to the detection of cancer biomarkers, other applications may be possible for the NME device, which may involve detecting DNA, RNA and/or proteins. Examples include profiling of breast cancer genes (e.g., by detecting RNA markers); profiling of leukemia-related genes (e.g., by detecting RNA markers); profiling of cytochrome P450 mutations that affect drug metabolism (e.g. Warfarin) (e.g., by detecting DNA and RNA markers); profiling of mutations associated with genetic disease (e.g. Cystic fibrosis) (e.g., by detecting DNA markers); detection and typing of viruses (e.g. HPV and HIV) (e.g., by detecting DNA and RNA markers); detection of cancer-related proteins using an electrochemical immunoassay format (e.g. prostate specific antigen (PSA)) (e.g., by detecting protein markers); and detection of micro RNAs to identify cancer. Biosensing devices incorporating these NMEs may be adapted to detect for these other biomolecules by binding suitable probes to the NME and/or by selecting a suitable electrocatalytic reaction to be sensed, as commonly known in the art.

It would be understood by a person skilled in the art that variations are possible without departing from the present disclosure. All examples and embodiments described are provided for the purpose of illustration only, and are not intended to be limiting. All references mentioned herein are hereby incorporated by reference in their entirety.

EXAMPLE 1

Parameters for Manufacturing NMEs

In this example, Pd was used as an electrode material. To investigate the time-dependence of the electrodeposition, the structures of the Pd NMEs being electrodeposited were monitored as a function of time. Time-dependent electrodeposition experiments were performed at −100 mV using 0.5 M HCl as supporting electrolyte. Pd structures were formed for (a) 25, (b) 50, (c) 125, (d) 250, and (e) 500 s. After 50 s, structures with average diameters of 1.3 µm and heights of 0.5 µm were observed, and after 500 s the Pd electrodes were typically 8 µm and 5 µm in diameter and height. The smaller structures made with shorter deposition times typically exhibited depressions in the center of the microelectrodes, which may indicate that nucleation occurs preferentially at the boundary of the aperture.

Another controllable parameter that may influence the final structure of the NME is the deposition potential. Specifically, the size and surface morphology of the NMEs may be controlled in this way. Dendritic fractals are phenomena generally observed in nonequilibrium growth such as the growth of snowflakes, the aggregation of soot particles, and the solidification of metals. Such fractal structures are also obtained by nonequilibrium electrodeposition of metals and used as model systems for the study of branching and fractal growth processes (Fleury, *Nature* 1997, 390, 145-148). It is generally believed that the morphology of crystals heavily depends on the "distance" of their formation conditions from the thermodynamic equilibrium: near-equilibrium conditions lead to polyhedral crystals surrounded with thermodynamically stable crystal faces, but increase of this "distance" makes the growing fronts of crystals with flat surfaces instable to form dendrites (Fukami et al. *J. Phys. Chem. C* 2007, 111, 1150-1160). In the case of electrodeposition of metals, such "distance" may be tuned continuously and reversibly by simply changing the deposition potential and more negative potential can exert higher driving force and thus increase the "distance" from the equilibrium for electrocrystallization. Thus, electrodeposition may be controlled spatially and kinetically to produce arrayed NMEs with varied well-defined morphologies.

Pd structures were formed at (a) 0 mV, (b) −100 mV, (c) −250 mV, and (d) −400 mV for 250 s with the use of 0.5 M HCl as supporting electrolyte. More negative deposition potentials were found to typically lead to larger, but less compact, microstructures. At a deposition potential of 0 mV, a cake-shaped structure of 3.5 µm diameter and 0.7 µm height was obtained. When the applied potential was changed to −100 mV, a rougher micro structure was obtained that was also larger in size (average diameter=5 µm and height=2.5 µm). The nanotexturing obtained is an irregular aggregate of very small nanoparticles. When a more negative potential of −250 mV was applied, a dendritic fractal micro structure was obtained and its diameter and height were found to further increase 11 and 6 µm, respectively. If the potential was increased further (e.g. to −400 mV), the microelectrode structure became more open and the structure is no longer continuous.

The electrochemical behaviour of the Pd NMEs formed as a function of potential was studied by cyclic voltammetry (CV). The electrochemical response of the NMEs was monitored in a solution containing 3 mM $Ru(NH_3)_6^{3+}$ and 0.09 M sodium phosphate, at a scan rate of 100 mV/s. As expected, steady-state voltammograms are observed for each electrode, consistent with the microscale dimensions of the electrodes. For the electrodes made using deposition potentials of 0, −100, or −250 mV, the currents observed are well-correlated with the size of the electrode. That is, the greater the diameter of the NME (i.e., formed at a larger applied potential), the greater the response current observed. However, for structures made at −400 mV, currents observed were lower than expected based on the size of the microelectrode, indicating that the discontinuity of the electrode structure may lead to poor electrical connectivity and loss of working area.

Thus, moderate deposition potentials appear to provide the most pronounced nanotexturing while maintaining the integrity of the resultant NME, as small nanoparticles are formed on the surface of the microelectrodes. It appears that providing too large of a driving potential for the deposition reaction accelerates the kinetics to a point where metal nanoparticles are formed without strong connectivity to the core of the NME.

NME morphology may also be controlled via electrolyte effects. Pd NMEs were formed at −100 mV for 250 s using (a) 0.5 M $H_2SO_4$ and (b) 0.5 M $HClO_4$ as the supporting electrolyte. These structures were formed under the same conditions as described above, where HCl was used as a supporting electrolyte. The structures formed in $H_2SO_4$ and $HClO_4$ were significantly larger than those formed in HCl, and interestingly, all three displayed different types of nanostructuring. NMEs made in $HClO_4$ showed the finest nanostructuring, with features as small as 10-20 nm present. In HCl, the electrode was more compact, and the nano structuring was on the order of 100 nm. The coarsest nanostructuring was obtained in $H_2SO_4$, where the particles comprising the electrode were larger than 200 nm. These observations indicate that the NME morphology may also be controlled by varying the supporting electrolyte used for electrodeposition.

Typically, the dendritic structures for the NME depend on the conditions during manufacture, including concentrations of the electrodeposition solution, choice of the metal to be electrodeposited, and the applied potential during electrodeposition. These parameters are readily controllable. For example, it may be desirable to control the concentration and purity of the reagents used in electrodeposition to within 5%. The choice of metal is simple to control as long as purity of the reagents is high, simply by obtaining the correct material. The potential during electrodeposition may be readily controlled to within a few mV, which is sufficient for controlling the size and morphology of the resultant NME.

EXAMPLE 2

Direct Profiling of Prostate Cancer Biomarkers in Tumor Tissue Using a Multiplexed Nanostructured Microelectrode Integrated Circuit Materials and Methods Chip Fabrication. The chips were fabricated at the Canadian Photonics Fabrication Center. 3" silicon wafers were passivated using a thick layer of thermally grown silicon dioxide. A 350 nm gold layer was deposited on the chip using electron-beam assisted gold evaporation. The gold film was patterned using standard photolithography and a lift-off process. A 500 nm layer of insulating silicon dioxide was deposited using chemical vapor deposition. 500 nm apertures were imprinted on the electrodes using standard photolithography, and 2 mm×2 mm bond pads were exposed using standard photolithography.

Fabrication of Nanostructured Microelectrodes. Chips were cleaned by rinsing in acetone, IPA, and DI water for 30 s and dried with a flow of nitrogen. All electrodeposition was performed at room temperature with a Bioanalytical Systems Epsilon potentiostat with a three-electrode system featuring an Ag/AgCl reference electrode and a platinum wire auxiliary electrode. 500 nm apertures on the fabricated electrodes were used as the working electrode and were contacted using the exposed bond pads. Platinum NMEs were fabricated in a platinum bath containing 5 mM solution of $H_2PtCl_6$ and 0.5 M $HClO_4$ at −250 mV for 10 s using DC potential amperometry.

Preparation and Purification of Oligonucleotides. All synthetic oligonucleotides were stringently purified by reversed-phase HPLC. The following probe and target sequences were used in experiments. Seq. P1. Type III fusion probe (PNA): $NH_2$-Cys-Gly-ATA AGG CTT CCT GCC GCG CT-$CONH_2$ (SEQ ID NO. 1), Seq. P2. Type I fusion probe (PNA): $NH_2$-Cys-Gly-CTG GAA TAA CCT GCC GCG CT-$CONH_2$ (SEQ ID NO. 2), Seq. P3. Type VI fusion probe (PNA): $NH_2$-Cys-Gly-ATA AGG CTT CTG AGT TCA AA-$CONH_2$ (SEQ ID NO. 3), Seq. T1 (Type III TMPRSS2:ERG fusion DNA target): 5'AGC GCG GCA GGA AGC CTT AT3' (SEQ ID NO. 4), Seq. T2 (WT TMPRSS2 DNA target): 5'AGC GCG GCA GGT CAT ATT GA3' (SEQ ID NO. 5), Seq. T3 (WT ERG DNA target): 5'TCA TAT CAA GGA AGC CTT AT3' (SEQ ID NO. 6), Seq. T4 (noncomplementary DNA target): 5'TTT TTT TTT TTT TTT TTT TT3' (SEQ ID NO. 7). Oligonucleotides were quantitated by measuring absorbance at 260 nm and ext. coefficients calculated using: http://www.idtdna.com/analyzer/Applications/OligoAnalyzer/.

Modification of NMEs with PNA Probes. A solution containing 500 nM thiolated single stranded PNA, 25 mM sodium phosphate (pH 7), and 25 mM sodium chloride was heated at 50° C. for 10 minutes. A suitable amount of 10 mM MCH was then added to make the final MCH concentration of 100 nM. 0.5-10 μL (depending on the degree of multiplexing) of this mixture was deposited on the NMEs in a dark humidity chamber overnight at 4° C. The NMEs were rinsed in 25 mM sodium phosphate (pH 7), and 25 mM NaCl buffer before measurement.

Electrochemical Measurements. Electrochemical signals were measured in solutions containing 10 μM $Ru(NH_3)_6^{3+}$, 25 mM sodium phosphate (pH 7), 25 mM sodium chloride, and 4 mM $Fe(CN)_6^{3-}$. Differential pulse voltammetry (DPV) signals before and after hybridization were measured using a potential step of 5 mV, pulse amplitude of 50 mV, pulse width of 50 ms, and a pulse period of 100 ms. Cyclic voltammetry signals before and after hybridization were collected with a scan rate of 100 mV/s. Limiting reductive current (I) was quantified by subtracting the background at 0 mV from the cathodic current at −300 mV in a cyclic voltammetry signal. Signal changes corresponding to hybridization were calculated as follows: $\Delta I = (I_{ds} - I_{ss})/I_{ss} \times 100\%$ (ss=before hybridization, ds=after hybridization).

Hybridization Protocol. Hybridization solutions typically contained target sequences in 25 mM sodium phosphate (pH 7), and 25 mM NaCl. Electrodes were incubated at 37° C. in humidity chamber in dark for 60 minutes and were washed extensively with buffer before electrochemical analysis.

Isolation of mRNA. The mRNAs were extracted from cell lines and patient tissue samples with the Dynabeads mRNA Direct Kit (Invitrogen). Two typical prostate cancer tissue samples were obtained from radical prostatectomies collected by from the Cooperative Human Tissue Network. The tissue was stored at −85° C. until tumor-rich tissue was selected for mRNA extraction. The concentrations of mRNA targets were measured by NanoDrop ND-1000 of Thermo Fisher Scientific (USA). All of the fusion sequences were confirmed by RT-PCR and direct sequencing.

Kinetic Measurements of DNA Hybridization at NMEs. PNA (seq. 2)-modified NMEs were prepared as described above. Rinsed NMEs were immersed in a solution containing 10 μM $Ru(NH_3)_6^{3+}$, 4 mM $Fe(CN)_6^{3-}$, 100 fM DNA target (seq.4 to 7), 25 mM sodium phosphate (pH 7), and 25 mM NaCl. The electrocatalytic CV signals were obtained as described above. All measurements were performed at 37° C.

Results and Discussions

We sought to generate a nanomaterial-based platform for ultrasensitive bioanalysis that is i) highly robust and straightforward to fabricate; ii) multiplexed and scalable; and iii) sensitive and specific when presented with heterogeneous biological samples. To satisfy requirements i) and ii) we required a means of achieving reproducible placement of each individual sensing element using a scalable protocol. To address requirement iii), we sought to incorporate nanoscale features into our sensing array. The production of arrayed nanostructured sensing elements, however, can be labor-intensive and prone to low reproducibility. Electron-beam lithography provides the needed control over nanoscale features and their placement; however, it is a serial technique not presently suited to low-cost, high-volume chip production. Our approach was instead to use cost-effective conventional photolithography to position and address our electrodes; and then find a means to bring about, with a high degree of reproducibility, the nanostructuring of these microelectrodes.

We constructed an 8-fold multiplexed chip by patterning a 350 nm thick gold layer on a silicon chip to create eight 5-μm-wide Au wires attached to large metal pads that would serve as external contacts. $SiO_2$ was then deposited as a passivating layer and patterned to create apertures with 500 nm diameters at the end of each of the Au wires. These openings were created to serve as individual templates for controlled, local growth of nanostructures. We then used palladium electrodeposition to deposit metal in the patterned apertures. We found that we were able to regulate the size of the nanostructures by varying the deposition time. We were readily able to confine the diameter of the structures to the ultramicroelectrode regime (<10 u). Under conditions enabling rapid metal deposition, the surfaces of the microelectrodes displayed a high level of nano structuring, with feature sizes of approximately 20 nm. These structures displayed ideal microelectrode behavior, exhibiting low capacitive currents and high steady-state plateau currents.

In order to make these nanostructured microelectrodes (NMEs) functional as nucleic acids biosensors, we modified them with thiolated peptide-nucleic acids (PNA) probes. The use of PNA as a probe molecule has been shown previously to increase the sensitivity of biosensing assays and is particularly advantageous in electrochemical assays because it produces lowered background currents. To transduce nucleic acids hybridization into an electrical signal, we employed an electrocatalytic reporter system previously developed by our laboratory. (Lapierre, M. A. et al., Anal. Chem. 2003, 75. 6327-6333). This reporter system relies on the accumulation of Ru(NH3)63+ at electrode surfaces when polyanionic species like nucleic acids bind, and the catalysis of the reduction of Fe(III) via the inclusion of Fe(CN)63−, which regenerates Ru(III) and allows multiple reductions per metal center. When PNA-modified NMEs were challenged with a complementary sequence, detectable signal changes could be clearly detected through the femtomolar concentration range. Negligible signal changes were observed with completely non-complementary sequences.

The cancer biomarkers selected for analysis on this platform are a group of gene fusions specific to prostate cancer. These fusions, resulting from a chromosomal translocation that joins the ERG and TMPRSS2 genes, were recently discovered and appear in at least 50% of prostate tumours. Furthermore, there are ~20 sequence types that feature different fusion sites, and the exact type of fusion present in a tumour appears to correlate with its aggressiveness and metastatic potential. These sequences are therefore not only promising diagnostic markers, but are also factors with prognostic value.

To determine whether the NME sensors could discriminate gene fusion sequences from the wild-type sequences that would be half-complementary, a sensor modified with a probe complementary to the splice site of the Type III fusion was challenged with: (1) the fusion target (seq. T1), (2) the sequence corresponding to the wild-type TMPRSS2 gene (seq. T2), and (3) a sequence corresponding to the wild-type ERG gene (seq. T3). A completely non-complementary control was also assayed (seq. T4). With a hybridization time of 60 minutes, large signal increases were observed with the fully complementary target, while a much lower signal change was seen with the TMPRSS2 target. The ERG target produced an even lower signal change, and that observed with the non-complementary sequence was negligible. The TMPRSS2 target binds to the portion of the probe located at the end of the sequence not attached to the electrode, while the ERG target binds to the portion of the probe located at the end tethered to the electrode surface. The different signal levels observed indicate that the most accessible side of the probe is better able to bind incoming target molecules, while hybridization with the more buried part of the sequence is inefficient.

To determine whether the hybridization of the different targets required the full 60 minute time period originally tested for accurate readout, the electrocatalytic signals were monitored at a variety of intervals within the window originally tested. Interestingly, the rise of the signals is very fast, with significant current changes observed within 2 minutes. Over the total 60-minute period, however, the signals for the half-complementary and non-complementary sequences fall noticeably; with 20-50% of the 2-minute signal vanishing by 60 minutes. It appears that for sequences that are not fully complementary, some nonspecific binding occurs in the first few minutes of exposure of the NME sensor to the target solution, but these complexes do not remain stable and do not remain immobilized on the electrode. Thus, while non-complementary sequences can be discriminated from complementary sequences with short hybridization times, longer times increase the differential signal changes, and thus the degree of specificity.

The performance of these nanostructured microelectrodes as nucleic acids detectors indicated that the patterned structures were indeed sensitive and specific when used under appropriate hybridization conditions. We therefore sought to prove that multiplexed chip-based NMEs could be used to assay cancer biomarkers presented in heterogeneous biological samples. To explore this capability, cell extracts and tumour samples from prostate cancer patients were assessed to determine whether the sensitivity and specificity of the system was robust enough for clinical testing.

To determine whether we could detect prostate-cancer associated gene fusions using the NME chip, we first analyzed mRNA isolated from two prostate cancer cell lines: VCaP and DU145. The former cell line is type III fusion positive, and the latter is fusion negative. No appreciable signal changes occurred when 10 ng of mRNA from the cell line that lacks this sequence were incubated with a NME displaying a probe complementary to the type III fusion (seq. PI), while large signal increases were observed in the presence of 10 ng mRNA from the cell line that does contain the type III fusion. In addition, the modification of NMEs with a probe complementary to a different fusion (seq. P2) did not yield a significant signal with positive mRNA sample. The detection of the fused gene is therefore highly specific. These results are significant, as efficiency in the use of sample (10 ng) and the total time required for analysis (less than 1.5 hours) significantly improve upon other detection methods like fluorescence in situ hybridization (FISH) and sequencing.

The ultimate application of the NME chip is the direct, multiplexed analysis of a panel of cancer biomarkers in relevant patient samples. To test the performance of our device for this type of application, we analyzed a panel of mRNA samples collected from cell lines and clinical tumor samples for a series of gene fusions. We obtained a group of samples that would allow the detection of the three most common types of prostate-cancer gene fusions: type I, type III, and type VI. Different clinical outcomes are associated with these sequences, with type III fusions being the most common but correlating with low cancer recurrence rates, whereas type I and VI fusions are correlated with aggressive cancers with high levels of recurrence. It is therefore of great interest to be able to differentiate these fusions in tumours, and a method that would permit their presence or absence to be assessed quickly and straightforwardly would be of value in their further study and validation as diagnostic biomarkers.

Probes complementary to each of the three fusions were deposited on their respective electrodes on NME chips, and 5 different mRNA samples were profiled for the presence of different gene fusions in a multiplexed format. Three cell lines were tested: VCap (type III positive),28 NCI-H660 (type III and VI positive)30, and DU145 (fusion negative).28 In addition, two tumour samples (tissues collected by radical prostatectomies) were tested, one that was positive for the type I fusion, and one that was positive for the type III fusion, as confirmed by conventional sequencing. In each case, all experiments took less than 2 hours and required only 10 ng of mRNA. By analyzing the electrochemical signals collected at NMEs displaying different probes, we ascertained the identity of fused genes present in each sample. For example, in the patient sample containing the type I fusion (as verified by sequencing), the current values observed at each probe-modified NME decreased in the following order: I>>>>III>VI. In the patient sample containing the type III fusion, the electronic signals again pointed to the correct identity of the fusion with probe III>>>>I>VI. These results, and those obtained with DU145, VCaP, and H660 cellular RNA, where electronic profiling correctly called the absence or presence of gene fusions, indicate that NME chips are able to profile these important biomarkers in complex samples and to distinguish biomarker profiles associated with different clinical outcomes.

The detection platform described here is not only specific, sensitive, and robust, it is also practical and scalable. The reproducible fabrication method we chose is amenable to the production of probe-modified chips using the same photo-lithographic technologies in widespread use in consumer electronics microchip fabrication; and only simple, inexpensive instrumentation is needed for readout. Microfluidics are not required for automated analysis, as hybridization can be performed and read out in a single reaction vessel. This system represents an attractive alternative to PCR-based methods that are sensitive but difficult to automate in a clinical setting.

In sum, the new multiplexed electrode platform we describe here is the first to read directly a panel of cancer biomarkers in clinically-relevant samples using electronic signals. The array enabling these measurements features microelectrodes that possess controllable and versatile nano-texturing essential for sensitivity. The system combines these nanotextured electrodes with rapid catalytic readout to achieve a long-standing goal: the multiplexed analysis of cancer biomarkers using an inexpensive and practical platform.

EXAMPLE 3

Direct, Electronic MicroRNA Detection Reveals Differential Expression Profiles in 30 Minutes Materials and Methods Materials. 6-mercapto-1-hexanol (97% MCH), hexaamine ruthenium chloride (99.9+%), potassium ferricyanide (99%), and palladium (II) chloride (99.9+%) were purchased from Sigma-Aldrich Canada Ltd (Oakville, ON), perchloric acid (70%), acetone (ACS grade) and isopropyl alcohol (IPA, ACS grade) were obtained from EMD (Gibbstown, N.J.). Thiolated PNA oligomers were obtained from Biosynthesis Inc (Lewisville, Tex.) with HPLC purified grade. PNA probes a Cys-Gly dipeptide at their N-terminus. Gly acts as a spacer, while Cys provides free thiol for immobilization on the electrode surface. Synthetic microRNAs (5' end phosphorylated and HPLC purified) were obtained from Euro fins MWG Operon (Huntsville, Ala.). All PNA and RNA sequences are shown in table S1 provided in the supporting information.

Chip Fabrication. The chips were fabricated at the Canadian Photonics Fabrication Center. 3" silicon wafers were passivated using a thick layer of thermally grown silicon dioxide. A 350 nm gold layer was deposited on the chip using electron-beam assisted gold evaporation. The gold film was patterned using standard photolithography and a lift-off process. A 500 nm layer of insulating silicon dioxide was deposited using chemical vapor deposition. 500 nm apertures were imprinted on the electrodes using standard photolithography, and 2 mm×2 mm bond pads were exposed using standard photolithography.

Fabrication of Nanostructured Microelectrodes. Chips were cleaned by rinsing in acetone, IPA, and DI water for 30 s and dried with a flow of nitrogen. All electrodeposition was performed at room temperature with a Bioanalytical Systems Epsilon potentiostat with a three-electrode system featuring an Ag/AgCl reference electrode and a platinum wire auxiliary electrode. 500 nm apertures on the fabricated electrodes were used as the working electrode and were contacted using the exposed bond pads. A 2 mm portion of the chip was immersed into the plating bath containing 5 mM palladium (II) chloride and 0.5 M perchloric acid, and incubated for about 5 min prior to electroplating. The bond pads were kept free from solution. Pd NMEs were fabricated using DC potential amperometry at an applied potential of −100 mV for 6 s.

Modification of NMEs with PNA Probes. Single-stranded thiolated PNA probes were dissolved in a buffer solution (pH 7) containing 25 mM sodium phosphate and 25 mM sodium chloride at a concentration of 500 nM. The solution was then heated at 50° C. for 10 minutes to fully dissolve the PNA molecules. A suitable amount of 10 mM MCH was then added to make the final MCH concentration of 100 nM. 10 µL of this mixture was quickly deposited on a chip displaying Pd NMEs using a manual micropipettor. This PNA probe>solution covered chip was then incubated in a dark humidity chamber overnight at 4° C. The probe-modified Pd NMEs were vigorously rinsed with the above buffer solution before measurements. For multiplexed experiments, chips with eight individually addressable leads were used.

Target Hybridization. Hybridization solutions contained various concentrations of targets in 25 mM sodium phosphate (pH 7.0) and 25 mM NaCl. Pd NMEs were incubated with 10 µL of target solution at 37° C. in a humidity chamber for 30 mins to allow the immobilized probe molecules to hybridize with target molecules. The chip was then cooled and washed vigorously with buffer before the electrochemical analysis.

Electrochemical Measurements. Electrochemical measurements were performed with an electrochemical analyzer (BASi, West Lafayette, USA) in a solution containing 10 mM Ru(NH3)6 3+, 4 mM Fe(CN)6 3−, 25 mM sodium phosphate (pH 7.0) and 25 mM NaCl. Cyclic voltammetry (CV) was conducted before and after the addition of target solutions at a scan rate of 100 mV/s. Differential pulse voltammetry (DPV) was performed at a potential step of 5 mV, pulse amplitude of 50 mV, pulse width of 50 ms and a pulse i period of 100 ms. Cyclic voltammetry signals before and after hybridization were collected with a scan rate of 100 mV/s. Limiting reductive current (I) was quantified by subtracting the background at 0 mV from the cathodic current at −300 mV in a cyclic voltammetry signal. Signal changes corresponding to hybridization were calculated as follows: $\Delta I=(Ids-Iss)/Iss\times100$ (ss=before hybridization, ds=after hybridization). The detection limit was determined as the first concentration where background (noncomplementary $\Delta I$) subtracted signal was 2 times higher than the standard deviation of 10 fM non-complementary control sample.

SEM Imaging. HITACHI S-3400 SEM (Hitachi High Technologies America, Inc., Pleasanton, Calif.) was employed to study the morphology and dimension of the electroplated [1] NMEs. The chip was affixed on a stainless steel SEM stub using doublesided adhesive black carbon tape. The SEM image was acquired using the secondary electron mode at 20 kV.

RNA Extraction for PCR Analyses and Amplification Protocol. Total RNA was extracted from cell lines with mirVana kit (Ambion). The quality of samples was assessed by RT-PCR analysis of the endogenous control RNU44 using Applied Biosystems TaqMan® microRNA Assay. This assay includes a reverse transcription (RT) step using the TaqMan® MicroRNA Reverse Transcription Kit (Applied Biosystems, CA, USA) wherein a stemloop RT primer specifically hybridizes to a mir molecule and is then reverse transcribed with a MultiScribe reverse transcriptase. Briefly, the reverse transcription mix includes 50 nM stemloop RT primers, 1×RT buffer, 0.25 mM each of dNTPs, 3.33 U/µL MultiScribe reverse transcriptase, and 0.25 U/µl RNase inhibitor. The 7.5 µL reaction was then incubated in an Applied Biosystems 7900 Thermocycler for 30 minutes at 16° C., 30 minutes at 42° C., 5 minutes at 85° C. and then held at 4° C. The RT products were subsequently amplified with sequence-specific primers (hsa-mir-21 primer 4373090, and hsa-mir-205 primer 4373093 from Applied Biosystems) using the Applied Biosystems 7900 HT Real-Time PCR system. The 10 μL PCR mix contains 0.67 μL RT product, 1×4 TaqMan® Universal PCR Master Mix, 0.2 μM Taq-Man® probe, 1.5 μM forward primer and 0.7 μM reverse primer. The reactions were incubated in a 384-well plate at 95° C. for 10 minutes followed by 40 cycles of 95° C. for 15 seconds and 60° C. for 1 minute.

Cloning and Expression of Pre-miRNA-21. cDNA was produced by reverse transcribing 500 ng total RNA from FaDu cells using High-Capacity cDNA Reverse Transcription Kit (Applied Biosystems) according to manufacturer's instructions. 50 ng of cDNA were used as template for PCR amplification of the premiRNA-21 stem loop with 1 μM of the primers MIR-F (CCT ACC ATC GTG AC A TCT CCA TGG) and MIR-R (ATG AGA ACA TTG GAT ATG GAT GGT). The conditions for the PCR were: 95° C. for 2 min, followed by 40 cycles of 95° C. for 1 min, 55° C. for 1 min, and 72° C. for 1 min, and a final extension step at 72° C. for 10 min. The PCR product was gel purified (Gel extraction kit, Qiagen) and cloned in pCR4-TOPO vector (invitrogen). Colonies were picked and grown in LB medium. Plasmid DNA was purified with Plasmid Mini Kit (Qiagen), and checked for the correct product, orientation, and absence of undesired mutations with sequencing (ACGT corporation). Plasmid DNA was digested with Not1 which does not generate 3' protruding ends that produce high background vector RNA during in vitro transcription. 1 μg of linearized plasmid DNA was used as a template for in vitro transcription with AmpliScribe™ T3 High Yield Transcription Kit (Epicentre Biotechnologies). After the completion of reverse transcription, DNase I was added to digest the template DNA and RNA was purified with PureLink Micro to Midi Total RNA Purification Kit (Invitrogen). Concentration of RNA was determined by reading the absorbance at 260 nm.

Results and Discussions

We endeavored to develop a new method for microRNA profiling that would feature the convenience of array-based analysis, but would augment the power of such multiplexing with the exceptional sensitivity required to assay small biological samples for low abundance microRNAs. Given that conventional fluorescence-based methods are insufficiently sensitive to monitor hybridization of small numbers of molecules to surface—bound probe sequences with simple instrumentation, we instead pursued an approach that employed electronic readout.

In order to provide a platform for electronic microRNA detection, a multiplexed chip was prepared that featured an electrode pattern generated by photolithography. This chip was made using a silicon wafer as a base, and a pattern of gold was deposited on its surface to provide a multiplexed set of leads and external contacts. A layer of SiO was deposited on top of the gold to passivate the metal, and then in the final fabrication step, 500 nanometer apertures were opened on the end of each lead to expose gold. To generate protruding microelectrodes, palladium was electrodeposited in the apertures. The electrodeposition step was engineered to produce highly nanostructured microelectrodes (NMEs). Previous studies have indicated that nano structured sensing elements can present biomolecular probes more efficiently than bulk materials and facilitate surface complexation reactions, but this advantage has never been exploited for direct biological profiling.

To test the electronic chip for sensitivity and specificity in microRNA detection, Pd NMEs were modified with PNA probes and exposed to RNA for hybridization. Complexation was assayed using a redox reporter system, previously shown to exhibit femtomolar sensitivity when used in conjunction with nanostructured electrodes and PNA probes. (R. Gasparac, et. al., J. Am. Chem. Soc. 2004, 126, 12270; Z. Fang, S. O. Kelley, Anal. Chem. 2009, 81, 612; M. A. Lapierre, et al., Anal. Chem. 2003, 75, 6327; M. A. Lapierre-Devlin, et al., Nano Lett. 2005, 5, 1051). This reporter system relies on the accumulation of Ru(III) when nucleic acids hybridize at an electrode surface, and the signals obtained from this reporter are amplified by the inclusion of ferricyanide, which can regenerate Ru(III) chemically after its electrochemical reduction. Titrations of the miR-21 sequence showed detectable signal changes relative to non-complementary control sequences when solutions containing as little as 10 aM of the target were exposed to the chip-based NMEs. This corresponds to 10 molecules per microliter of sample. The very high level of sensitivity is accompanied by a limited dynamic range of only $10^2$, but for the detection of microRNAs, this tradeoff is merited given the low abundance of these sequences.

Two crucial additional sensing criteria are specifically demanded in microRNA detection. First, closely related sequences—different by as few as one base—must be accurately distinguished. Second, sequence appendages like those found in mature vs. precursor microRNAs, must be discriminated. We sought to challenge our system with each of these requirements. We investigated first the specificity of the assay for mature microRNA sequences. This was conducted by analyzing signal changes observed when the chip was exposed to solutions containing either the full-length, double-stranded, precursor form of miR-21, or the significantly shorter, single-stranded, mature miR-21 sequence. The signal obtained for the hairpin precursor structure approached background levels, while a robust signal change was observed for mature miR-21.

We evaluated the sensitivity of the detection approach to point mutations by monitoring the response of probe-modified sensing elements to two closely related sequences, miR-26a and miR-26b. Probes complementary to each sequence were arrayed on the chip, and the response of these elements to the complementary sequences was monitored. The signal obtained when miR-26a was introduced was approximately 4 times for the fully matched miR-26a probe over the mismatched miR-26b probe, and similarly, the signal obtained when miR-26b was introduced was approximately 4.5-fold higher for the fully matched miR-26b probe over its mismatched counterpart probe. These results indicate that this multiplexed chip can successfully discriminate closely related microRNA sequences.

Deriving a "fingerprint" of microRNA expression from cell lines representing a particular tumour type relative to normal cells has been previously shown to be a powerful approach to identify microRNAs that can serve as biomarkers in patients. Having confirmed the specificity and sensitivity of the chip towards microRNA targets, we then tested it using RNA samples extracted from human normal cells and those derived from human head and neck squamous cancer cell lines grown in culture. For example, total RNA extracted from the human hypopharyngeal squamous cancer FaDu cell line and a normal oral epithelial cell line was titrated onto a nanostructured microelectrode displaying a probe complementary to miR-205. A positive signal was obtained with as little as 5 ng of RNA derived from the FaDu cells, while normal epithelial cells did not produce any signal change with up to 20 ng of RNA. This indicates that the signal response corresponds to a unique marker present at significantly higher levels in the cancer cell lines.

We profiled two different microRNAs, miR-21 and miR-205, and also included a control RNA, RNU-44 in a panel of total RNA samples. We employed three different head and neck squamous cancer cell lines, and compared the response of the microelectrode chip to these total RNA samples relative to RNA isolated from normal oral epithelial cells. As expected, RNU-44 levels, as judged by the electrochemical response measured for each total RNA sample exposed to a sensing element modified with a complementary probe, remained constant in all four cell lines. However, miR-21 and miR-205 signals were both significantly elevated in the cancer cell lines. Indeed, the levels of these microRNAs were judged to be present at >100-fold higher levels in the cancer cell lines relative to the normal epithelial cells. The over-expression of these targets was confirmed using conventional quantitative PCR (see supporting information). Both miR-21 and miR-205 have been previously observed to be elevated in primary human head and neck squamous carcinomas, indicating a significant potential for these micro-RNAs to serve as diagnostic biomarkers for this malignancy.

In conclusion, the microRNA detection chip described here offers the sensitivity and specificity for the analysis of a novel class of nucleic acids biomarkers representing one of the most challenging detection targets. Electronic readout of microRNA profiles offers a rapid—yet highly accurate—method to directly assay RNA samples for specific sequences, and the lack of labeling or amplification renders this approach to be extremely straightforward and efficient, features not attainable with other PCR or hybridization-based approaches.

The invention claimed is:

1. A biosensing workstation comprising: a cartridge holder for holding a biosensing cartridge, the biosensing cartridge including a sample chamber for containing a biological sample and a biosensing chamber containing a biosensing device, the biosensing device including:
   a substrate;
   an electrically conductive lead on the substrate;
   an insulating layer covering the lead, the insulating layer having an aperture exposing a portion of the lead;
   a nanostructured microelectrode, the microelectrode in electrical communication with the exposed portion of the lead, the microelectrode adapted to generate a charge in response to a biomolecular stimulus; and
   a charge storage in electrical communication with the lead for storing charge from the microelectrode, the charge on the charge storage at the end of an integration period indicative of the biomolecular stimulus;
   an instrument tip for accessing the biosensing cartridge;
   a selection mechanism for selecting a biosensing process to be carried out;
   a processor adapted to carry out the biosensing process using the biosensing cartridge and to determine results of the biosensing process from electronic signals generated from the biosensing cartridge; and
   a display for displaying the results of the biosensing process.

2. The workstation of claim 1, wherein there is a plurality of cartridge holders for holding a plurality of biosensing cartridges.

3. The workstation of claim 1, wherein the instrument tip is disposable.

4. The workstation of claim 1, further comprising a bar code reader for uniquely identifying the biosensing cartridge.

5. The workstation of claim 1, further comprising a waste chamber for containing waste products from the biosensing process.

6. The workstation of claim 1, wherein the workstation is capable of wireless communication through a wireless network.

7. The biosensing workstation of claim 1, wherein the lead comprises a material selected from the group consisting of: Au, Al, W, TiN, and polysilicon.

8. The biosensing workstation of claim 1, wherein the substrate comprises a material selected from the group consisting of: silicon, silica, quartz, glass, sapphire, gallium arsenide, germanium, silicon carbide, indium compounds, selenium sulfide, ceramic, plastic, polycarbonate and other polymer or combinations of any of the above.

9. The biosensing workstation of claim 1, wherein the insulating layer is comprised of a material selected from the group consisting of: silicon dioxide, silicon nitride, nitrogen doped silicon oxide, and parylene or combinations of any of the above.

10. The biosensing workstation of claim 1, wherein the aperture has an approximate diameter in the range of about 100 nm to about 10 μm.

11. The biosensing workstation of claim 1, wherein the biosensing device further comprises a display component for displaying the charge stored in the charge storage.

12. The biosensing workstation of claim 1, wherein the biosensing device further comprises a transistor.

13. The biosensing workstation of claim 12, wherein the transistor is a field-effect transistor (FET).

14. The biosensing workstation of claim 13, wherein the FET is selected from the group consisting of: an n-type silicon channel and a p-type silicon channel.

15. The biosensing workstation of claim 14, wherein the bipolar transistor is selected from the group consisting of: an n-p-n bipolar junction transistor, and a p-n-p bipolar junction transistor.

16. The biosensing workstation of claim 12, wherein the transistor is a bipolar transistor.

17. The biosensing workstation of claim 1, wherein the biosensing device comprises a plurality of leads, each having a respective microelectrode.

18. The biosensing workstation of claim 17, wherein the biosensing device comprises at least two different probe molecules provided on the microelectrodes.

19. The biosensing workstation of claim 1, wherein the microelectrodes are provided in an array, and each microelectrode is individually electronically accessible.

20. The biosensing workstation of claim 1, wherein the biosensing chamber is adapted to subdivide the biological sample through chemical, mechanical or vibrational means.

21. The biosensing workstation of claim 1, wherein the biosensing cartridge further comprises a purifying chamber for purifying or isolating the sample.

22. The biosensing workstation of claim 1, wherein the biosensing cartridge further comprises a lid having capsules, the capsules containing reagents for carrying out the biosensing process.

23. The biosensing workstation of claim 22, wherein one of the capsules is associated with the sample chamber, the capsule containing a lysis buffer reagent.

24. The workstation of claim 23, further comprising a bar code reader for uniquely identifying the biosensing cartridge.

25. The biosensing workstation of claim 1, wherein the biosensing cartridge is disposable.

26. A biosensing workstation comprising: a cartridge holder for holding a biosensing cartridge, the biosensing cartridge including a sample chamber for containing a biological sample and a biosensing chamber containing a biosensing device, the biosensing device including:
   a substrate;
   an electrically conductive lead on the substrate;
   an insulating layer covering the lead, the insulating layer having an aperture exposing a portion of the lead;
   a nanostructured microelectrode, the microelectrode being in electrical communication with the exposed portion of the lead, the microelectrode being adapted to generate a charge in response to a biomolecular stimulus; and
   a charge storage in electrical communication with the lead for storing charge from the microelectrode, the charge on the charge storage at the end of an integration period indicative of the biomolecular stimulus;
   an instrument tip for accessing the biosensing cartridge;
   a processor adapted to carry out a biosensing process using the biosensing cartridge and to determine results of the biosensing process from electronic signals generated from the biosensing cartridge; and
   a display for displaying the results of the biosensing process.

27. The workstation of claim 26, wherein there is a plurality of cartridge holders for holding a plurality of biosensing cartridges.

28. The workstation of claim 26, wherein the instrument tip is disposable.

29. The workstation of claim 26, further comprising a waste chamber for containing waste products from the biosensing process.

30. The workstation of claim 26, wherein the workstation is capable of wireless communication through a wireless network.

31. The biosensing workstation of claim 26, wherein the lead comprises a material selected from the group consisting of: Au, Al, W, TiN, and polysilicon.

32. The biosensing workstation of claim 26, wherein the substrate comprises a material selected from the group consisting of: silicon, silica, quartz, glass, sapphire, gallium arsenide, germanium, silicon carbide, indium compounds, selenium sulfide, ceramic, plastic, polycarbonate and other polymer or combinations of any of the above.

33. The biosensing workstation of claim 26, wherein the insulating layer is comprised of a material selected from the group consisting of: silicon dioxide, silicon nitride, nitrogen doped silicon oxide, and parylene or combinations of any of the above.

34. The biosensing workstation of claim 26, wherein the aperture has an approximate diameter in the range of about 100 nm to about 10 µm.

35. The biosensing workstation of claim 26, wherein the biosensing device further comprises a display component for displaying the charge stored in the charge storage.

36. The biosensing workstation of claim 26, wherein the biosensing device further comprises a transistor.

37. The biosensing workstation of claim 36, wherein the transistor is a field-effect transistor (FET).

38. The biosensing workstation of claim 37, wherein the FET is selected from the group consisting of: an n-type silicon channel and a p-type silicon channel.

39. The biosensing workstation of claim 38, wherein the bipolar transistor is selected from the group consisting of: an n-p-n bipolar junction transistor, and a p-n-p bipolar junction transistor.

40. The biosensing workstation of claim 36, wherein the transistor is a bipolar transistor.

41. The biosensing workstation of claim 26, wherein the biosensing device comprises a plurality of leads, each having a respective microelectrode.

42. The biosensing workstation of claim 41, wherein the biosensing device comprises at least two different probe molecules provided on the microelectrodes.

43. The biosensing workstation of claim 26, wherein the microelectrodes are provided in an array, and each microelectrode is individually electronically accessible.

44. The biosensing workstation of claim 26, wherein the biosensing chamber is adapted to subdivide the biological sample through chemical, mechanical or vibrational means.

45. The biosensing workstation of claim 26, wherein the biosensing cartridge further comprises a purifying chamber for purifying or isolating the sample.

46. The biosensing workstation of claim 26, wherein the biosensing cartridge further comprises a lid having capsules, the capsules containing reagents for carrying out the biosensing process.

47. The biosensing workstation of claim 46, wherein one of the capsules is associated with the sample chamber, the capsule containing a lysis buffer reagent.

48. The biosensing workstation of claim 26, wherein the biosensing cartridge is disposable.

* * * * *

UNITED STATES PATENT AND TRADEMARK OFFICE
CERTIFICATE OF CORRECTION

PATENT NO. : 10,274,453 B2
APPLICATION NO. : 15/703120
DATED : April 30, 2019
INVENTOR(S) : Leyla Soleymani et al.

Page 1 of 1

It is certified that error appears in the above-identified patent and that said Letters Patent is hereby corrected as shown below:

In the Claims

Claim 15, Column 26, Line numbers 37-40:
Delete "The biosensing workstation of claim 14, wherein the bipolar transistor is selected from the group consisting of: an n-p-n bipolar junction transistor, and a p-n-p bipolar junction transistor." and insert -- The biosensing workstation of claim 12, wherein the transistor is a bipolar transistor. --

Claim 16, Column 26, Line numbers 41-42:
Delete "The biosensing workstation of claim 12, wherein the transistor is a bipolar transistor." and insert -- The biosensing workstation of claim 15, wherein the bipolar transistor is selected from the group consisting of: an n-p-n bipolar junction transistor, and a p-n-p bipolar junction transistor. --

Claim 39, Column 28, Line numbers 18-21:
Delete "The biosensing workstation of claim 38, wherein the bipolar transistor is selected from the group consisting of: an n-p-n bipolar junction transistor, and a p-n-p bipolar junction transistor." and insert -- The biosensing workstation of claim 36, wherein the transistor is a bipolar transistor. --

Claim 40, Column 28, Line numbers 22-23:
Delete "The biosensing workstation of claim 36, wherein the transistor is a bipolar transistor." and insert -- The biosensing workstation of claim 39, wherein the bipolar transistor is selected from the group consisting of: an n-p-n bipolar junction transistor, and a p-n-p bipolar junction transistor. --

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*